United States Patent
Yokoyama et al.

(10) Patent No.: US 10,541,369 B2
(45) Date of Patent: Jan. 21, 2020

(54) COMPOUND HAVING SUBSTITUTED BIPYRIDYL GROUP AND PYRIDOINODOLE RING STRUCTURE, AND ORGANIC ELECTROLUMINESCENT DEVICE

(75) Inventors: Norimasa Yokoyama, Tokyo (JP); Daizou Kanda, Tokyo (JP); Shuichi Hayashi, Tokyo (JP); Eiji Takahashi, Tsukuba (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 410 days.

(21) Appl. No.: 13/979,746

(22) PCT Filed: Jan. 16, 2012

(86) PCT No.: PCT/JP2012/000206
§ 371 (c)(1),
(2), (4) Date: Jul. 15, 2013

(87) PCT Pub. No.: WO2012/098849
PCT Pub. Date: Jul. 26, 2012

(65) Prior Publication Data
US 2013/0292663 A1    Nov. 7, 2013

(30) Foreign Application Priority Data
Jan. 18, 2011  (JP) .................. 2011-007458

(51) Int. Cl.
*H01L 51/50* (2006.01)
*H01L 51/00* (2006.01)
*C07D 471/04* (2006.01)
*C07D 401/14* (2006.01)

(52) U.S. Cl.
CPC ........ *H01L 51/0072* (2013.01); *C07D 401/14* (2013.01); *C07D 471/04* (2013.01); *H01L 51/0067* (2013.01); *H01L 51/5072* (2013.01); *H01L 51/5096* (2013.01)

(58) Field of Classification Search
CPC ............ H01L 51/0072; H01L 51/0067; H01L 51/5072; H01L 51/5096; C07D 471/04; C07D 471/02; C07D 401/00; C07D 401/02; C07D 401/10; C07D 401/14; C07D 403/00; C07D 403/02; C07D 403/10; C07D 403/14; C07D 211/04; C07D 221/00; C09K 11/06; C09K 2211/1018; C09K 2211/1029; C09K 2211/1044; C09K 2211/1074; C09K 2211/1059
USPC ..... 546/85, 87, 256, 257; 548/440; 428/690, 428/691, 917; 427/58, 66; 313/500–512;
(Continued)

(56) References Cited

U.S. PATENT DOCUMENTS

| | | | |
|---|---|---|---|
| 8,252,431 B2 * | 8/2012 | Yokoyama | C07D 471/04 257/40 |
| 2004/0086745 A1 * | 5/2004 | Iwakuma | C07D 401/10 428/690 |

(Continued)

FOREIGN PATENT DOCUMENTS

| | | |
|---|---|---|
| CN | 101663300 A | 3/2010 |
| EP | 1571193 A1 | 9/2005 |

(Continued)

OTHER PUBLICATIONS

Fukagawa et al., "Pyridoindole Derivative as Electron Transporting Host Material for Effi cient Deep-blue Phosphorescent Organic Light-emitting Diodes", 2010, Advanced Materials, vol. 22, pp. 4775-4778.*

(Continued)

*Primary Examiner* — Andrew K Bohaty
*Assistant Examiner* — Dylan C Kershner
(74) *Attorney, Agent, or Firm* — Locke Lord LLP; James E. Armstrong, IV; Nicholas J. DiCeglie, Jr.

(57) ABSTRACT

To provide an organic compound of excellent characteristics that exhibits excellent electron-injecting/transporting performance with hole blocking ability, and has high stability in the thin-film state, as material for an organic electroluminescent device having high efficiency and high durability, and to provide the organic electroluminescent device having high efficiency and high durability using the compound. An organic electroluminescent device includes a pair of electrodes, and one or more organic layers sandwiched between the pair of electrodes, wherein the compound of general formula (1) in which a substituted bipyridyl group and a pyridoindole ring structure are bonded via a phenylene group, is used as a constituent material of at least one organic layer.

[Chemical Formula 1]

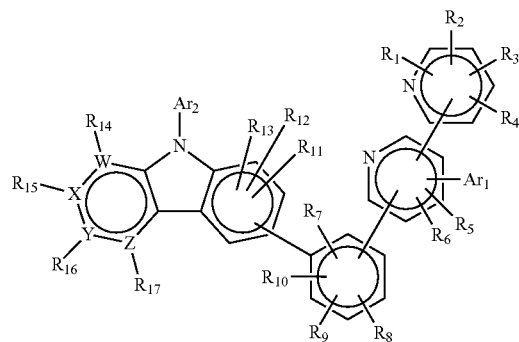

8 Claims, 2 Drawing Sheets

(58) Field of Classification Search
USPC .............. 257/40, 88–104, E51.001–E51.052; 252/301.16–301.35
See application file for complete search history.

(56) References Cited

U.S. PATENT DOCUMENTS

| | | | |
|---|---|---|---|
| 2006/0251918 A1* | 11/2006 | Iwakuma | H01L 51/0067 428/690 |
| 2007/0104976 A1* | 5/2007 | Iwakuma | C09K 11/06 428/690 |
| 2009/0021146 A1* | 1/2009 | Iida | C07D 209/86 313/504 |
| 2010/0123388 A1* | 5/2010 | Yokoyama | C07D 471/04 313/504 |
| 2011/0006291 A1 | 1/2011 | Yokoyama et al. | |
| 2012/0306358 A1* | 12/2012 | Hirano | C08G 61/12 313/504 |
| 2013/0049571 A1* | 2/2013 | Anryu | C08G 61/12 313/498 |
| 2014/0230900 A1* | 8/2014 | Cull | H01L 51/0007 136/263 |

FOREIGN PATENT DOCUMENTS

| | | |
|---|---|---|
| EP | 2128159 A1 | 12/2009 |
| JP | 2006-080271 A | 3/2006 |
| TW | 200938543 A | 9/2009 |
| WO | WO-2004/053019 A1 | 6/2004 |
| WO | WO-2008/114690 A1 | 9/2008 |

OTHER PUBLICATIONS

Supplementary European Search Report dated May 13, 2014, issued for the European patent application No. 12736240.8.
International Search Report dated Feb. 21, 2012, issued for PCT/JP2012/000206.
Office Action dated Dec. 3, 2014, issued for the corresponding Chinese patent application No. 201280005776.1 and Japanese translation thereof.
Office Action dated May 19, 2015, issued for the corresponding Taiwanese patent application No. 101101798 and Japanese translation thereof.

* cited by examiner

[Fig. 1]
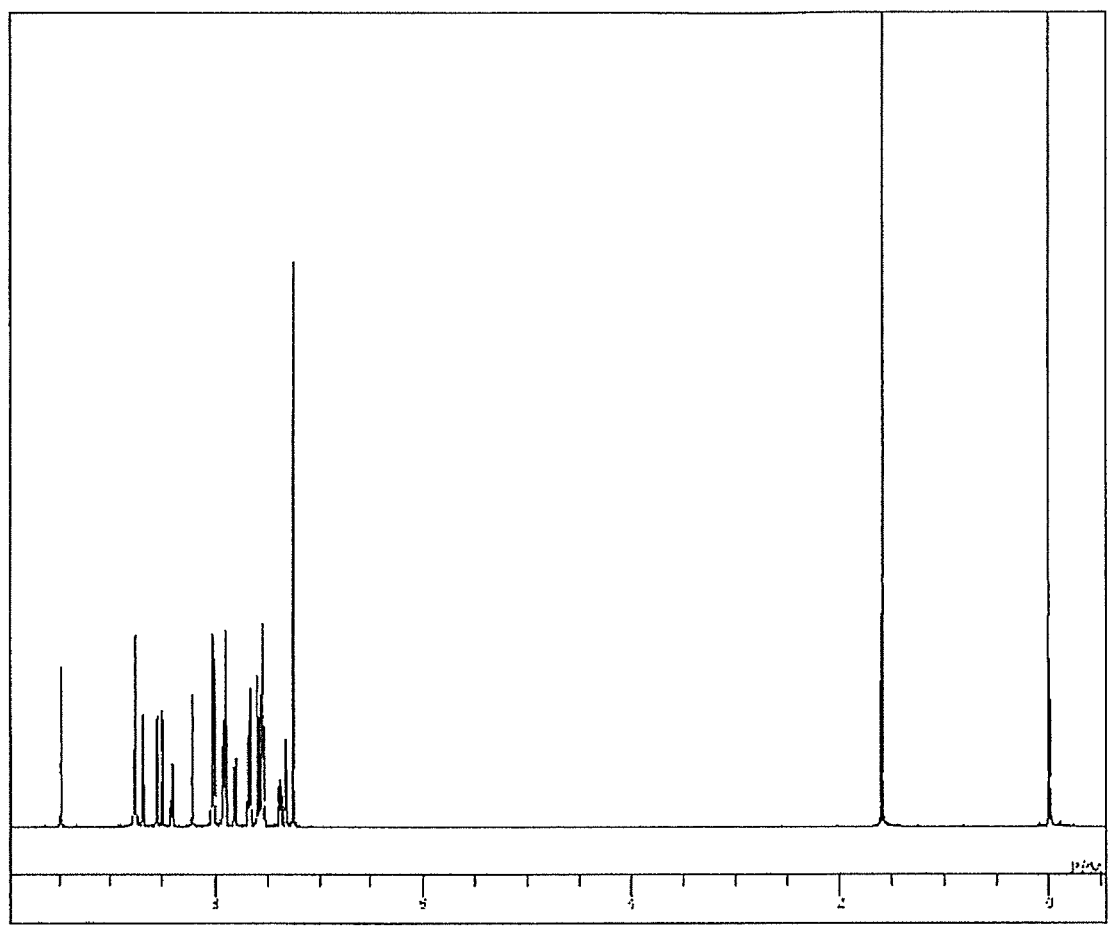

[Fig. 2]
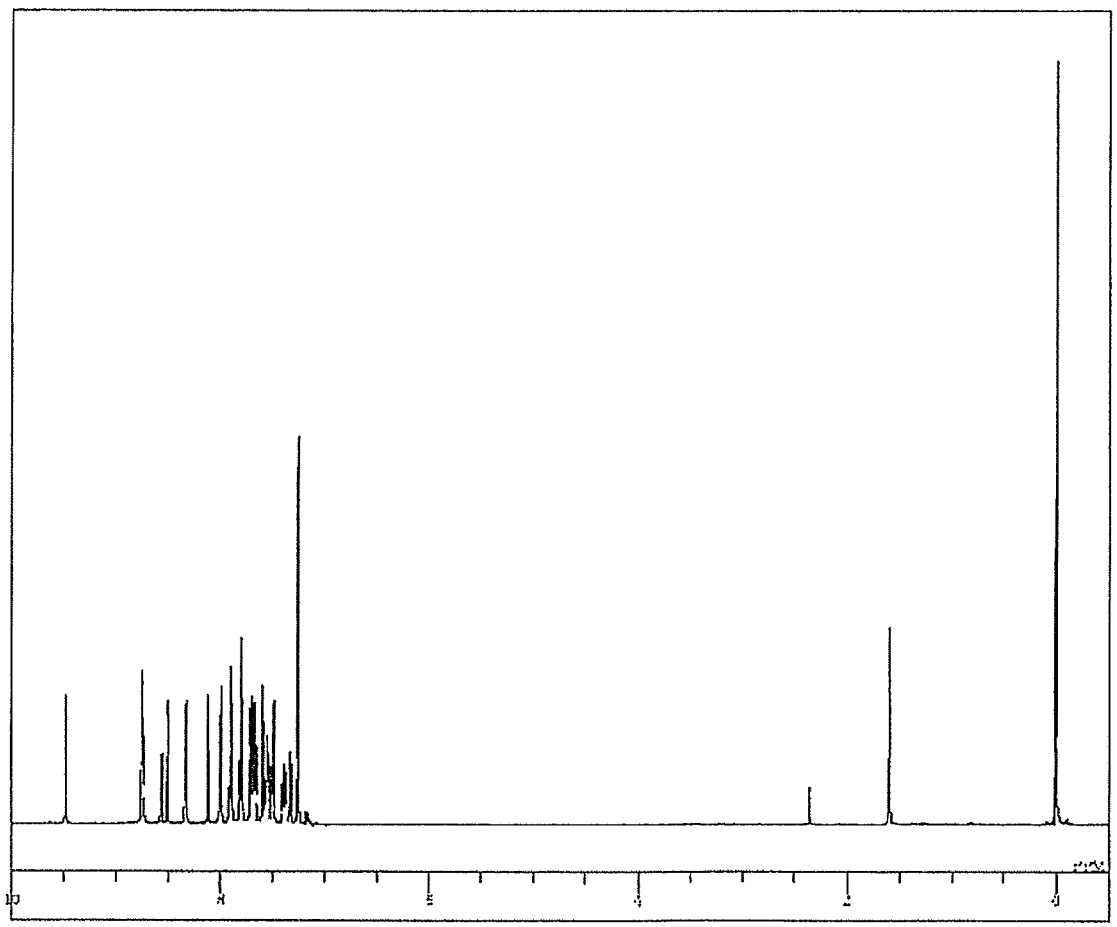
[Fig. 3]
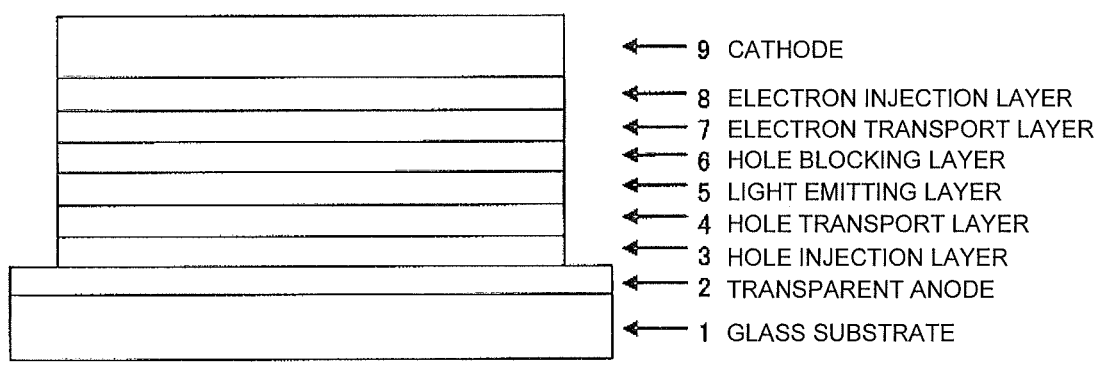
← 9 CATHODE
← 8 ELECTRON INJECTION LAYER
← 7 ELECTRON TRANSPORT LAYER
← 6 HOLE BLOCKING LAYER
← 5 LIGHT EMITTING LAYER
← 4 HOLE TRANSPORT LAYER
← 3 HOLE INJECTION LAYER
← 2 TRANSPARENT ANODE
← 1 GLASS SUBSTRATE

COMPOUND HAVING SUBSTITUTED BIPYRIDYL GROUP AND PYRIDOINODOLE RING STRUCTURE, AND ORGANIC ELECTROLUMINESCENT DEVICE

TECHNICAL FIELD

The present invention relates to compounds suitable for an organic electroluminescent device (hereinafter referred to as an organic EL device), a preferred self light-emitting device for various display devices, and to organic EL devices that use the compounds. Specifically, the invention relates to compounds in which a substituted bipyridyl group and a pyridoindole ring structure are bonded via a phenylene group, and to organic EL devices that use the compounds.

BACKGROUND ART

The organic EL device is a self-emitting device, and has been actively studied for their brighter, superior viewability and ability to display clearer images compared with the liquid crystal device.

In 1987, C. W. Tang et al. at Eastman Kodak developed a laminated structure device using materials assigned with different roles, realizing practical applications of an organic EL device with organic materials. These researchers laminated an electron-transporting phosphor and a hole-transporting organic material, and injected the both charges into the phosphor layer to cause emission in order to obtain a high luminance of 1,000 cd/m² or more at a voltage of 10 V or less (refer to Patent Documents 1 and 2, for example).

To date, various improvements have been made for practical applications of the organic EL device. In order to realize high efficiency and durability, various roles are further subdivided to provide an electroluminescent device that includes an anode, a hole injection layer, a hole transport layer, a light emitting layer, an electron transport layer, an electron injection layer, and a cathode sequentially formed on a substrate (refer to Non-Patent Document 1, for example).

Further, there have been attempts to use triplet excitons for further improvements of luminous efficiency, and use of phosphorescent materials has been examined (refer to Non-Patent Document 2, for example).

The light emitting layer can also be fabricated by doping a charge-transporting compound, generally called a host material, with a phosphor or a phosphorescent material. As described in the foregoing Non-Patent Documents 1 and 2, selection of organic materials in an organic EL device greatly influences various device characteristics, including efficiency and durability.

In an organic EL device, the charges injected from the both electrodes recombine at the light emitting layer to cause emission. However, because the hole mobility is faster than the electron mobility, some of the holes pass through the light emitting layer. This causes a problem of lowering efficiency. There is therefore a need for an electron transport material with fast electron mobility.

Tris(8-hydroxyquinoline)aluminum (hereinafter referred to as Alq$_3$), a representative light-emitting material, is generally used also as an electron transport material. However, with slow electron mobility and a work function of 5.6 eV, the material cannot be said to have sufficient hole blocking performance.

Insertion of a hole blocking layer is one method of preventing the passage of some of the holes through the light emitting layer and improving the probability of charge recombination at the light emitting layer. Examples of the hole blocking materials proposed so far include triazole derivatives (refer to Patent Document 3, for example), bathocuproin (hereinafter referred to as BCP), and a mixed ligand complex of aluminum [aluminum(III) bis(2-methyl-8-quinolinate)-4-phenylphenolate (hereinafter referred to as BAlq)] (refer to Non-Patent Document 2, for example).

On the other hand, 3-(4-biphenylyl)-4-phenyl-5-(4-t-butylphenyl)-1,2,4-triazole (hereinafter referred to as TAZ) is proposed as an electron transport material having excellent hole blocking performance (refer to Patent Document 3, for example).

TAZ has a large work function of 6.6 eV and a high hole blocking ability, and is thus used as an electron-transporting hole blocking layer laminated on the cathode side of a fluorescent layer or a phosphorescent layer produced by methods such as vacuum vapor deposition and coating. TAZ thus contributes to attaining the high efficiency of an organic EL device (refer to Non-Patent Document 3, for example).

However, TAZ has a big problem of poor electron transportability and needed to be combined with an electron transport material having higher electron transportability for the production of an organic EL device (refer to Non-Patent Document 4, for example).

BCP has a large work function of 6.7 eV and a high hole blocking ability. However, the low glass transition point (Tg) of 83° C. makes the thin film stability poor, and the material cannot be said to be sufficiently functional as a hole blocking layer.

Either of the materials lacks film stability, or has a function insufficient to block the holes. In order to improve the characteristics of an organic EL device, there is a need for an organic compound that exhibits excellent electron-injecting/transporting performance with high hole blocking ability, and has high stability in the thin-film state.

Compounds having an anthracene ring structure and a benzimidazole ring structure are proposed as compounds improved in the above aspects (refer to Patent Document 4, for example).

However, while the devices using these compounds for the electron injection layer or/and the electron transport layer have been improved in luminous efficiency and the like, the improvements are still insufficient. Further improvement for a lower driving voltage, higher luminous efficiency, and particularly higher current efficiency are therefore needed.

CITATION LIST

Patent Documents

Patent Document 1: JP-A-8-048656
Patent Document 2: Japanese Patent Number 3194657
Patent Document 3: Japanese Patent Number 2734341
Patent Document 4: WO2003/060956

Non-Patent Documents

Non-Patent Document 1: The Japan Society of Applied Physics, 9th lecture preprints, pp. 55 to 61 (2001)
Non-Patent Document 2: The Japan Society of Applied Physics, 9th lecture preprints, pp. 23 to 31 (2001)
Non-Patent Document 3: The 50th Applied Physics-Associated Joint Lecture Presentation, 28p-A-6, Lecture Preprints, p. 1413 (2003)

Non-Patent Document 4: The Japan Society of Applied Physics, Molecular Electronics and Bioelectronics Journal, Vol. 11, No. 1, pp. 13 to 19 (2000)
Non-Patent Document 5: J. Chem. Soc., Perkin Trans. 1, 1505 (1999)
Non-Patent Document 6: J. Org. Chem., 60, 7508 (1995)
Non-Patent Document 7: Synth. Commun., 11, 513 (1981)
Non-Patent Document 8: Synthesis, 1 (1976)

SUMMARY OF THE INVENTION

Problems that the Invention is to Solve

It is an object of the present invention to provide an organic compound of excellent characteristics that exhibits excellent electron-injecting/transporting performance with hole blocking ability, and has high stability in the thin-film state, as material for an organic EL device having high efficiency and high durability. The invention also provides an organic EL device of high efficiency and high durability using the compound.

The physical properties of the organic compound to be provided by the present invention include (1) good electron injection characteristics, (2) fast electron mobility, (3) excellent hole blocking ability, (4) stability in the thin-film state, and (5) excellent heat resistance. The physical properties, of the organic EL device to be provided by the present invention include (1) high luminous efficiency and high power efficiency, (2) low turn on voltage, and (3) low actual driving voltage.

Means for Solving the Problems

In order to achieve the foregoing objects, the present inventors have noted that a nitrogen atom of an electrophilic pyridine ring has the ability to coordinate with metal, that the pyridoindole ring structure has high electron transport ability, and that the pyridine ring and the pyridoindole ring structure are excellent in heat resistance, etc., and have planned and chemically synthesized a compound in which a substituted bipyridyl group and a pyridoindole ring structure are bonded via a phenylene group. The present inventors have used the compound to produce various organic EL devices experimentally, and as a result of having assiduously evaluated the characteristics of the devices, the present inventors have completed the present invention.

Specifically, the present invention is a compound of the following general formula (1) in which a substituted bipyridyl group and a pyridoindole ring structure are bonded via a phenylene group.

[Chemical Formula 1]

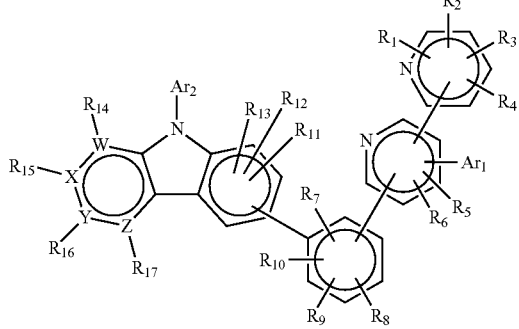

(1)

In the formula, $Ar_1$ and $Ar_2$ may be the same or different, and represent a substituted or unsubstituted aromatic hydrocarbon group, a substituted or unsubstituted aromatic heterocyclic group, or a substituted or unsubstituted condensed polycyclic aromatic group. $R_1$ to $R_{17}$ may be the same or different, and represent a hydrogen atom, a deuterium atom, a fluorine atom, a chlorine atom, cyano, trifluoromethyl, linear or branched alkyl of 1 to 6 carbon atoms, a substituted or unsubstituted aromatic hydrocarbon group, a substituted or unsubstituted aromatic heterocyclic group, or a substituted or unsubstituted condensed polycyclic aromatic group. W, X, Y, and Z represent a carbon atom or a nitrogen atom, where only one of W, X, Y, and Z is a nitrogen atom, and, in this case, the nitrogen atom does not have the hydrogen atom or substituent for $R_{14}$ to $R_{17}$.

Further, the present invention is a compound of the following general formula (1') in which a substituted bipyridyl group and a pyridoindole ring structure are bonded via a phenylene group.

[Chemical Formula 2]

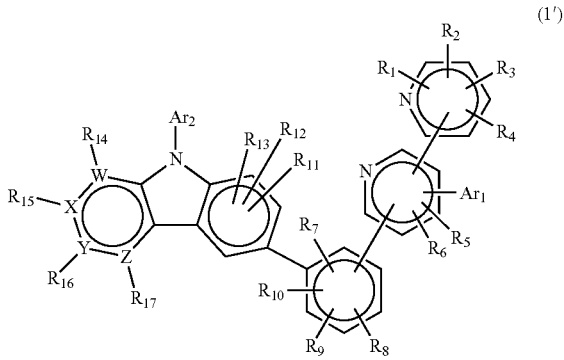

(1')

In the formula, $Ar_1$ and $Ar_2$ may be the same or different, and represent a substituted or unsubstituted aromatic hydrocarbon group, a substituted or unsubstituted aromatic heterocyclic group, or a substituted or unsubstituted condensed polycyclic aromatic group. $R_1$ to $R_{17}$ may be the same or different, and represent a hydrogen atom, a deuterium atom, a fluorine atom, a chlorine atom, cyano, trifluoromethyl, linear or branched alkyl of 1 to 6 carbon atoms, a substituted or unsubstituted aromatic hydrocarbon group, a substituted or unsubstituted aromatic heterocyclic group, or a substituted or unsubstituted condensed polycyclic aromatic group. W, X, Y, and Z represent a carbon atom or a nitrogen atom, where only one of W, X, Y, and Z is a nitrogen atom, and, in this case, the nitrogen atom does not have the hydrogen atom or substituent for $R_{14}$ to $R_{17}$.

Further, the present invention is a compound of the following general formula (1") in which a substituted bipyridyl group and a pyridoindole ring structure are bonded via a phenylene group.

[Chemical Formula 3]

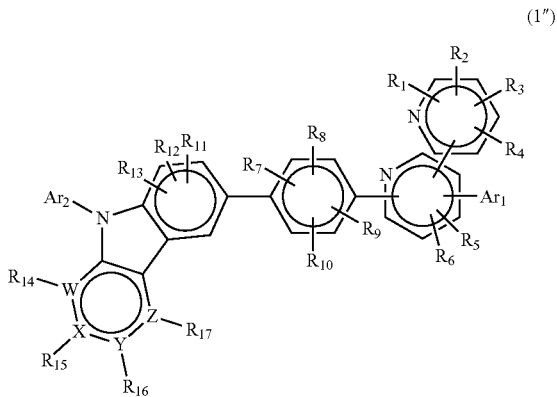

(1")

In the formula, $Ar_1$ and $Ar_2$ may be the same or different, and represent a substituted or unsubstituted aromatic hydrocarbon group, a substituted or unsubstituted aromatic heterocyclic group, or a substituted or unsubstituted condensed polycyclic aromatic group. $R_1$ to $R_{17}$ may be the same or different, and represent a hydrogen atom, a deuterium atom, a fluorine atom, a chlorine atom, cyano, trifluoromethyl, linear or branched alkyl of 1 to 6 carbon atoms, a substituted or unsubstituted aromatic hydrocarbon group, a substituted or unsubstituted aromatic heterocyclic group, or a substituted or unsubstituted condensed polycyclic aromatic group. W, X, Y, and Z represent a carbon atom or a nitrogen atom, where only one of W, X, Y, and Z is a nitrogen atom, and, in this case, the nitrogen atom does not have the hydrogen atom or substituent for $R_{14}$ to $R_{17}$.

Further, the present invention is an organic EL device that includes a pair of electrodes, and at least one organic layer sandwiched between the pair of electrodes, wherein the at least one organic layer contains the compound of the general formula (1), general formula (1'), or general formula (1") in which a substituted bipyridyl group and a pyridoindole ring structure are bonded via a phenylene group.

Specific examples of the "aromatic hydrocarbon group", "aromatic heterocyclic group", or "condensed polycyclic aromatic group" in the "substituted or unsubstituted aromatic hydrocarbon group", "substituted or unsubstituted aromatic heterocyclic group", or "substituted or unsubstituted condensed polycyclic aromatic group" represented by $Ar_1$ or $Ar_2$ in the general formula (1), (1'), or (1") include phenyl, biphenylyl, terphenylyl, tetrakisphenyl, styryl, naphthyl, anthryl, acenaphthenyl, phenanthryl, fluorenyl, indenyl, pyrenyl, pyridyl, triazinyl, pyrimidyl, furanyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, naphthyridinyl, phenanthrolinyl, and acridinyl.

Specific examples of the "substituent" in the "substituted aromatic hydrocarbon group", "substituted aromatic heterocyclic group", or "substituted condensed polycyclic aromatic group" represented by $Ar_1$ or $Ar_2$ in the general formula (1), (1'), or (1") include a deuterium atom, a fluorine atom, a chlorine atom, cyano, trifluoromethyl, hydroxyl, nitro, linear or branched alkyl of 1 to 6 carbon atoms, cyclopentyl, cyclohexyl, linear or branched alkoxy of 1 to 6 carbon atoms, dialkylamino groups substituted with linear or branched alkyl of 1 to 6 carbon atoms, phenyl, naphthyl, anthryl, fluorenyl, styryl, pyridyl, pyridoindolyl, quinolyl, and benzothiazolyl. These substituents may be further substituted.

$Ar_1$ in the general formula (1), (1'), or (1") is preferably the "substituted or unsubstituted aromatic hydrocarbon group" or "substituted or unsubstituted condensed polycyclic aromatic group", particularly preferably a substituted or unsubstituted phenyl, naphthyl, anthryl or fluorenyl group.

$Ar_2$ in the general formula (1), (1'), or (1") is preferably the "substituted or unsubstituted aromatic hydrocarbon group", particularly preferably a substituted or unsubstituted phenyl group.

Specific examples of the "aromatic hydrocarbon group", "aromatic heterocyclic group", or "condensed polycyclic aromatic group" in the "substituted or unsubstituted aromatic hydrocarbon group", "substituted or unsubstituted aromatic heterocyclic group", or "substituted or unsubstituted condensed polycyclic aromatic group" represented by $R_1$ to $R_{17}$ in the general formula (1), (1'), or (1") include phenyl, biphenylyl, terphenylyl, tetrakisphenyl, styryl, naphthyl, anthryl, acenaphthenyl, phenanthryl, fluorenyl, indenyl, pyrenyl, pyridyl, triazinyl, pyrimidyl, furanyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, naphthyridinyl, phenanthrolinyl, and acridinyl.

The "substituted or unsubstituted aromatic heterocyclic group" represented by $R_1$ to $R_4$ is preferably a substituted or unsubstituted pyridyl group, and an improvement in electron injection characteristics can be expected.

Specific examples of the "substituent" in the "substituted aromatic hydrocarbon group", "substituted aromatic heterocyclic group", or "substituted condensed polycyclic aromatic group" represented by $R_1$ to $R_{17}$ in the general formula (1), (1'), or (1") include a deuterium atom, a fluorine atom, a chlorine atom, trifluoromethyl, linear or branched alkyl of 1 to 6 carbon atoms, phenyl, biphenylyl, terphenylyl, tetrakisphenyl, styryl, naphthyl, fluorenyl, phenanthryl, indenyl, pyrenyl, and pyridoindolyl. These substituents may be further substituted.

Specific examples of the "linear or branched alkyl of 1 to 6 carbon atoms" represented by $R_1$ to $R_{17}$ in the general formula (1), (1'), or (1") include methyl, ethyl, n-propyl, i-propyl, n-butyl, i-butyl, t-butyl, n-pentyl, i-pentyl, t-pentyl, n-hexyl, i-hexyl, and t-hexyl.

A bipyridyl group in the compound of the general formula (1), (1'), or (1") of the present invention, in which a substituted bipyridyl group and a pyridoindole ring structure are bonded via a phenylene group is preferably a 2,3'-bipyridyl group from the viewpoint of heat resistance.

The compound of the general formula (1), (1'), or (1") of the present invention, in which a substituted bipyridyl group and a pyridoindole ring structure are bonded via a phenylene group, is a novel compound that secures faster electron movement than conventional electron transport materials, has an excellent hole-blocking ability and is stable as a thin film.

The compound of the general formula (1), (1'), or (1") of the present invention, in which a substituted bipyridyl group and a pyridoindole ring structure are bonded via a phenylene group, can be used as a constituent material of the electron injection layer and/or electron transport layer of an organic EL device. The use of the material having higher electron injectability and mobility than the conventional materials has effects of improving the electron transport efficiency from the electron transport layer to the light emitting layer to improve the luminous efficiency while lowering a driving voltage to improve the durability of the organic EL device.

The compound of the general formula (1), (1'), or (1") of the present invention, in which a substituted bipyridyl group and a pyridoindole ring structure are bonded via a phenylene group, can also be used as a constituent material of the hole blocking layer of an organic EL device. The use of the material having an excellent hole blocking ability and superior electron transportability and higher stability in the thin-film state than the conventional material has effects of lowering the driving voltage and improving the current resistance while maintaining high luminous efficiency, thereby improving the maximum emission luminance of the organic EL device.

The compound of the general formula (1), (1'), or (1") of the present invention, in which a substituted bipyridyl group and a pyridoindole ring structure are bonded via a phenylene group, can also be used as a constituent material of the light emitting layer of an organic EL device. The material of the present invention having superior electron transportability and a wider band gap than the conventional materials can be used as the host material of the light emitting layer, and a fluorescent material or phosphorescent material called a dopant is supported to form the light emitting layer. An organic EL device having a low driving voltage and improved luminous efficiency can thereby be achieved.

The organic EL device of the present invention uses the compound in which a substituted bipyridyl group and a pyridoindole ring structure are bonded via a phenylene group, wherein the compound has faster electron movement and superior hole blocking ability than the conventional electron transport materials while having a stable thin-film state. High efficiency and high durability can thereby be achieved.

Effects of the Invention

The compound of the present invention in which a substituted bipyridyl group and a pyridoindole ring structure are bonded via a phenylene group, is useful as a constituent material of the electron injection layer, electron transport layer, hole blocking layer, or light emitting layer of an organic EL device. The compound has an excellent hole blocking ability while having a stable thin-film state. The organic EL device of the present invention has high luminous efficiency and high power efficiency, and as a result, the actual driving voltage of the device can be lowered. Further, turn on voltage can be lowered to improve durability.

BRIEF DESCRIPTION OF THE DRAWINGS

FIG. 1 is a $^1$H-NMR chart of the compound of Example 1 of the present invention (Compound 2).
FIG. 2 is a $^1$H-NMR chart of the compound of Example 2 of the present invention (Compound 8).
FIG. 3 is a diagram illustrating the configuration of the EL devices of Examples 5 to 6 and Comparative Example 1.

MODE FOR CARRYING OUT THE INVENTION

The compounds of the present invention in which a substituted bipyridyl group and a pyridoindole ring structure are bonded via a phenylene group are novel compounds that may be synthesized, for example, as follows. First, a corresponding halogenoanilinopyridine is subjected to a cyclization reaction using a palladium catalyst to synthesize a corresponding pyridoindole derivative (refer to Non-Patent Document 5, for example), and various aromatic hydrocarbon compounds, condensed polycyclic aromatic compounds, or aromatic heterocyclic compounds are subjected to a condensation reaction such as an Ullmann reaction or a Buchward-Hartwig reaction with halides to synthesize a pyridoindole derivative substituted with an aryl group at the corresponding 5-position. The pyridoindole derivative substituted with the aryl group at the corresponding 5-position is brominated with N-bromosuccinimide or the like to synthesize a corresponding bromo compound. The corresponding bromo compound is then borated using bis(pinacolato)diboron or the like to synthesize a corresponding borate (refer to Non-Patent Document 6, for example). Further, the corresponding borate and various halogenophenylene having a bipyridyl group are subjected to a cross-coupling reaction such as Suzuki coupling (refer to Non-Patent Document 7, for example) to synthesize the compounds in which a substituted bipyridyl group and a pyridoindole ring structure are bonded via a phenylene group. The various halogenophenylene having a bipyridyl group may be synthesized by condensing a corresponding aldehyde and acetylpyridine in the presence of a base and further reacting with a corresponding pyridinium iodide (refer to Non-Patent Document 8, for example).

The following presents specific examples of preferred compounds among the compounds of general formula (1), (1'), or (1") of the present invention, in which a substituted bipyridyl group and a pyridoindole ring structure are bonded via a phenylene group. The present invention, however, is not restricted to these compounds.

[Chemical Formula 4]

(Compound 2)

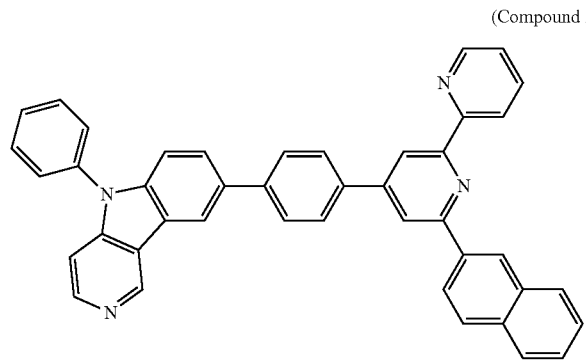

[Chemical Formula 5]

(Compound 3)

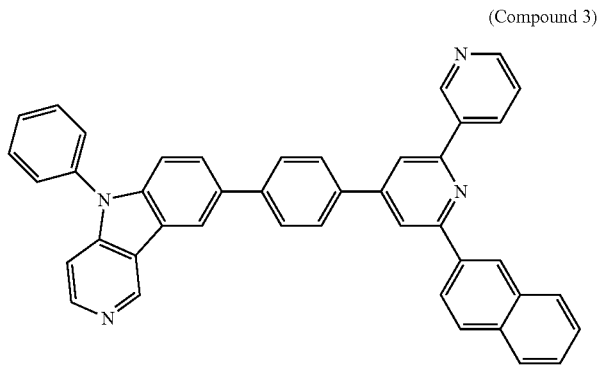

-continued
[Chemical Formula 6]
(Compound 4)
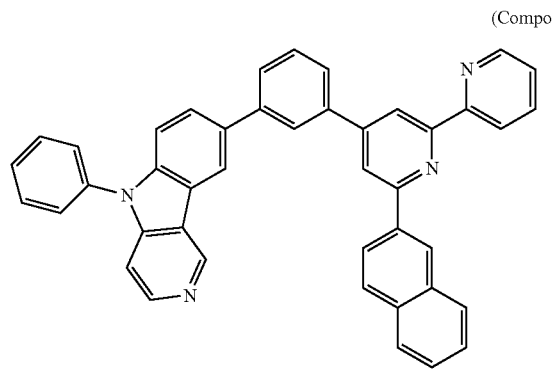
[Chemical Formula 7]
(Compound 5)
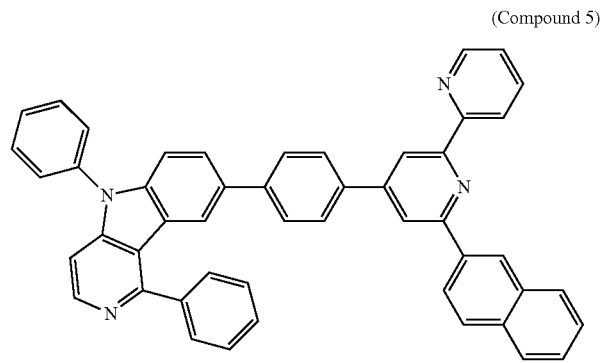
[Chemical Formula 8]
(Compound 6)
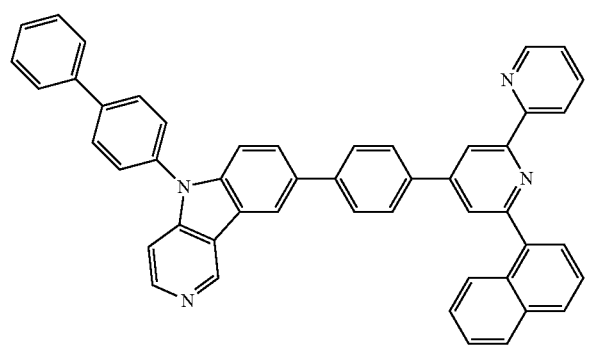
[Chemical Formula 9]
(Compound 7)
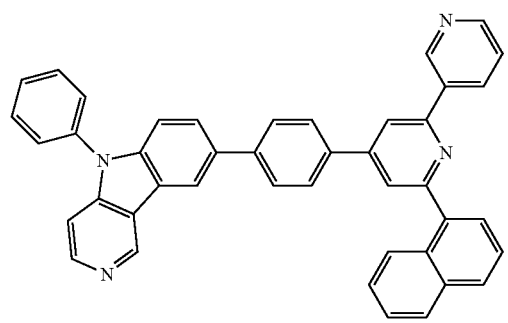
[Chemical Formula 10]
(Compound 8)
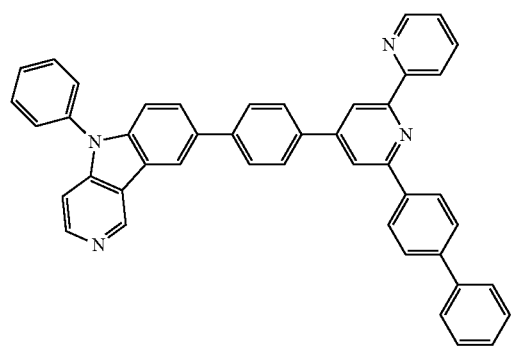
[Chemical Formula 11]
(Compound 9)
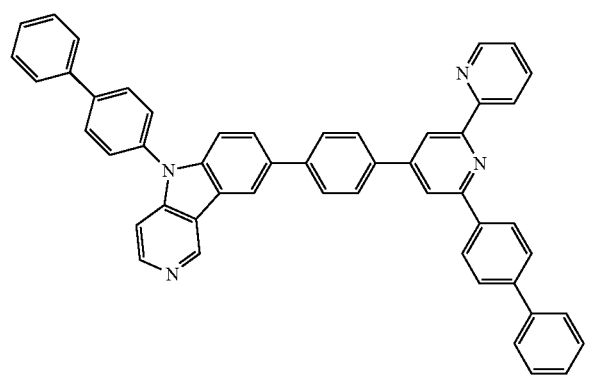

-continued
[Chemical Formula 12]
(Compound 10)
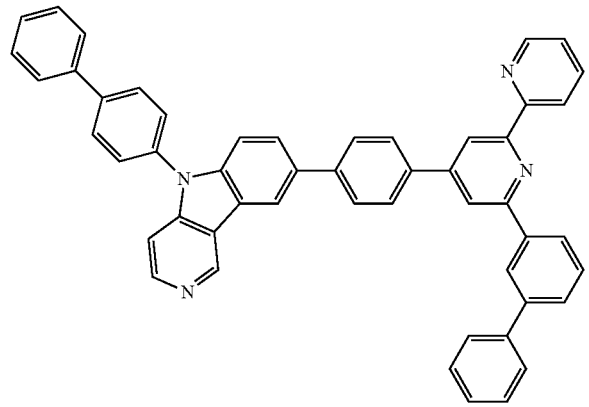
[Chemical Formula 13]
(Compound 11)
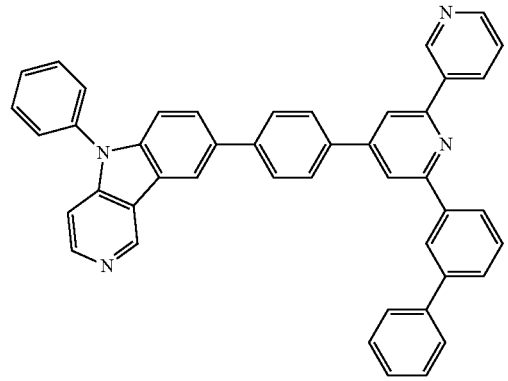
[Chemical Formula 14]
(Compound 12)
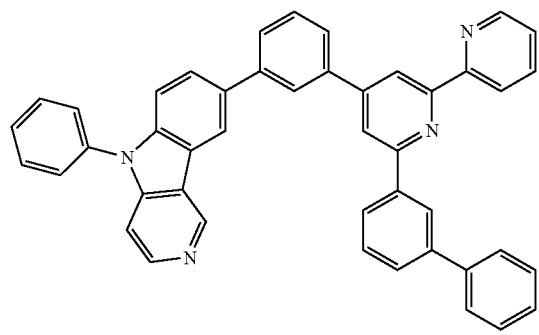
{Chemical Formula 15]
(Compound 13)
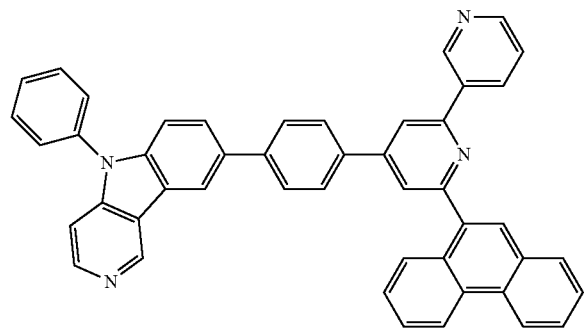
[Chemical Formula 16]
(Compound 14)
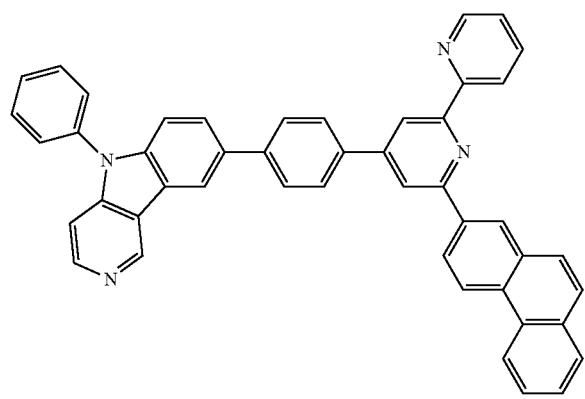
[Chemical Formula 17]
(Compound 15)
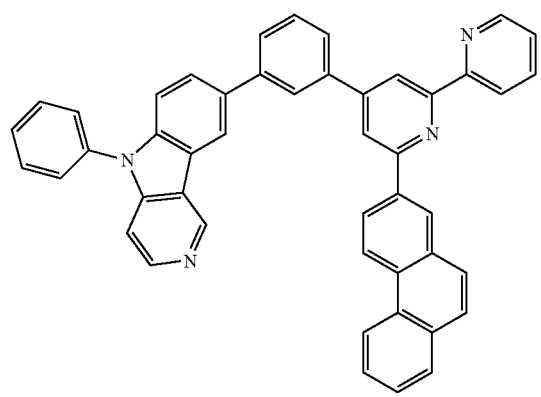

[Chemical Formula 18]
(Compound 16)
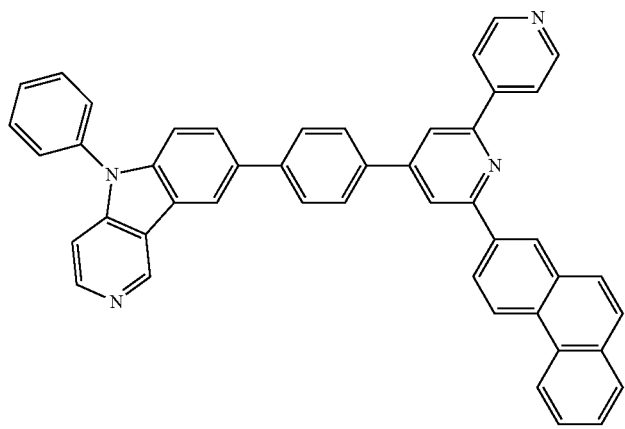
[Chemical Formula 19]
(Compound 17)
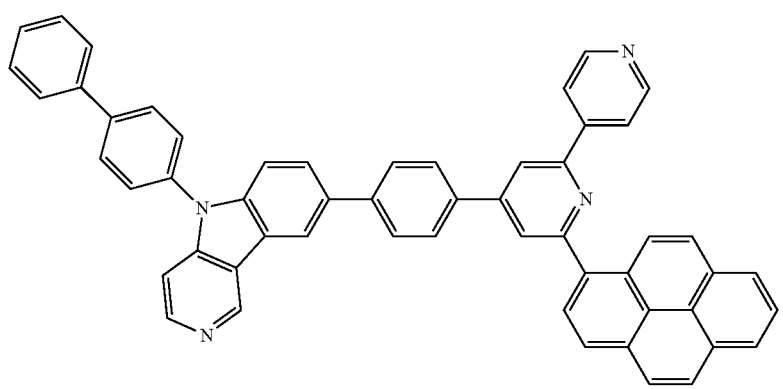
[Chemical Formula 20]
(Compound 18)
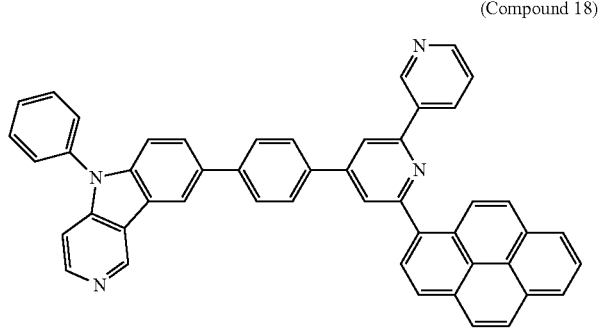
[Chemical Formula 21]
(Compound 19)
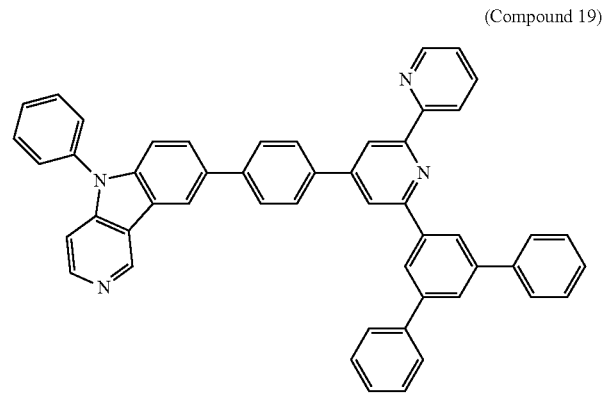

-continued
[Chemical Formula 22]
(Compound 20)
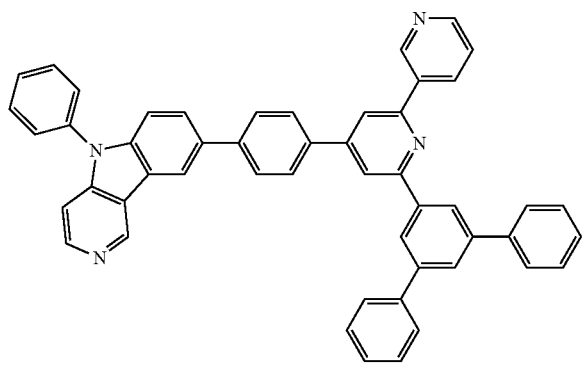
[Chemical Formula 23]
(Compound 21)
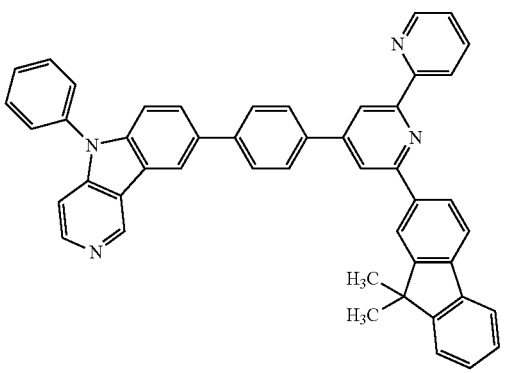
[Chemical Formula 24]
(Compound 22)
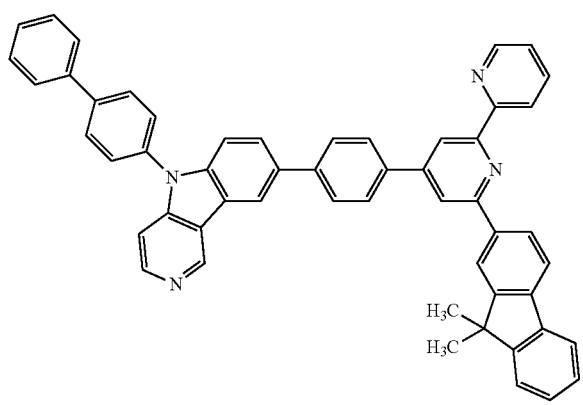
[Chemical Formula 25]
(Compound 23)
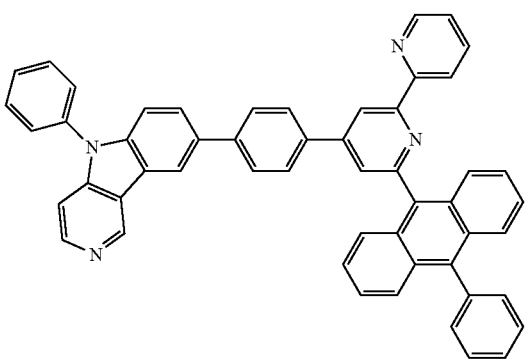
[Chemical Formula 26]
(Compound 24)
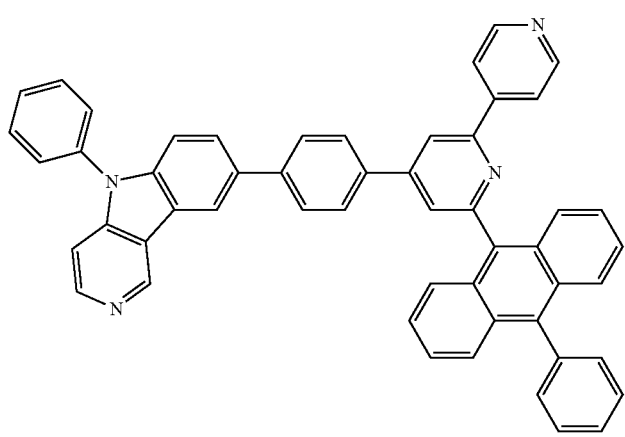

-continued
[Chemical Formula 27]
(Compound 25)
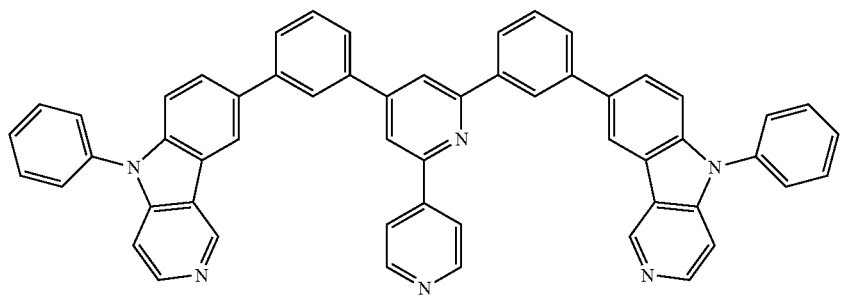
[Chemical Formula 28]
(Compound 26)
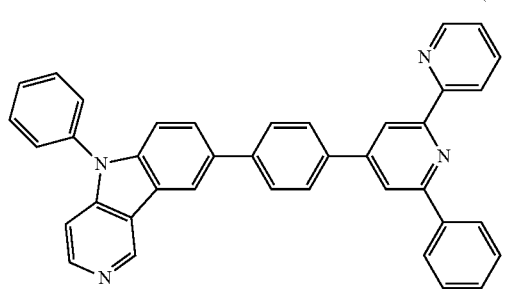
[Chemical Formula 29]
(Compound 27)
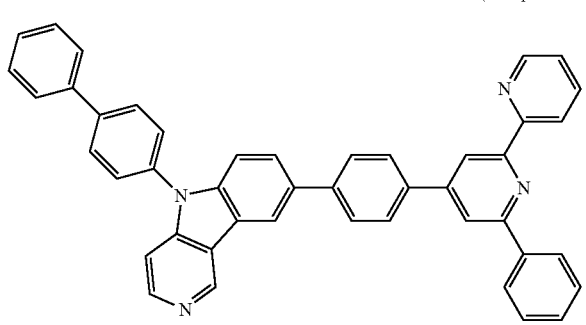
[Chemical Formula 30]
(Compound 28)
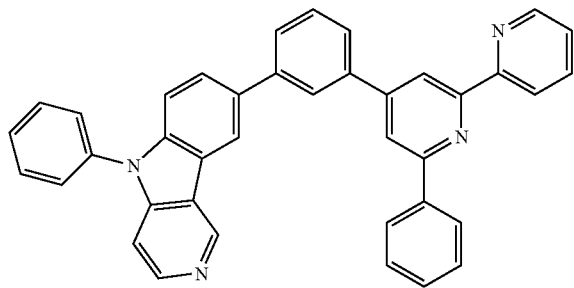
[Chemical Formula 31]
(Compound 29)
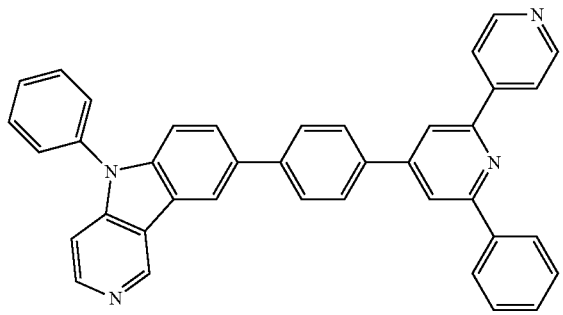
[Chemical Formula 32]
(Compound 30)
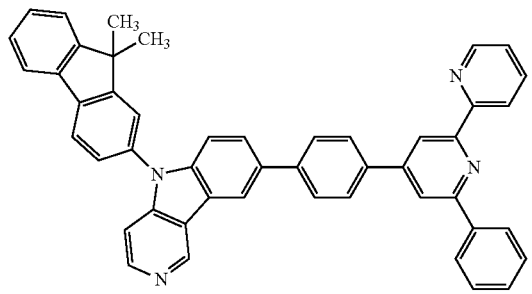
[Chemical Formula 33]
(Compound 31)
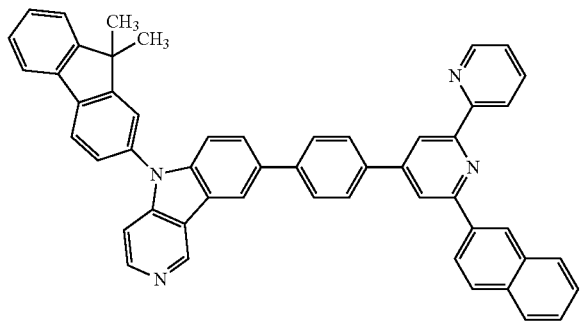

-continued
[Chemical Formula 34]
(Compound 32)
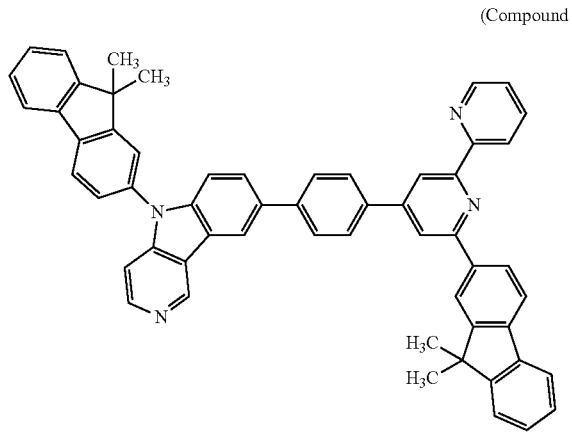
[Chemical Formula 35]
(Compound 33)
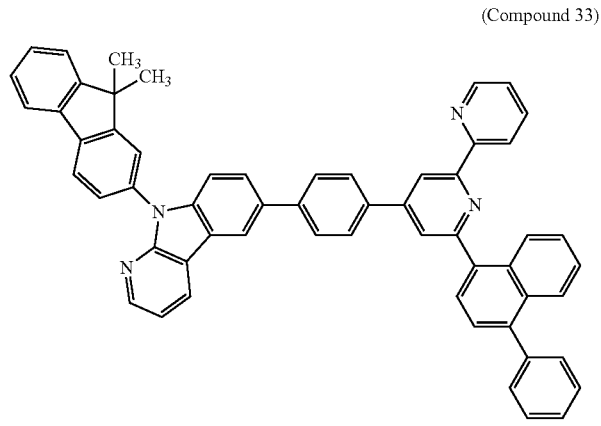
[Chemical Formula 36]
(Compound 34)
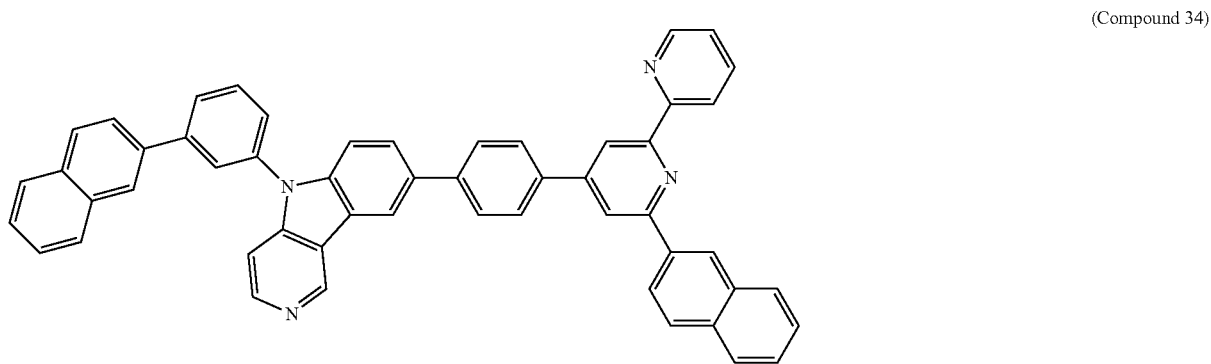
[Chemical Formula 37]
(Compound 35)
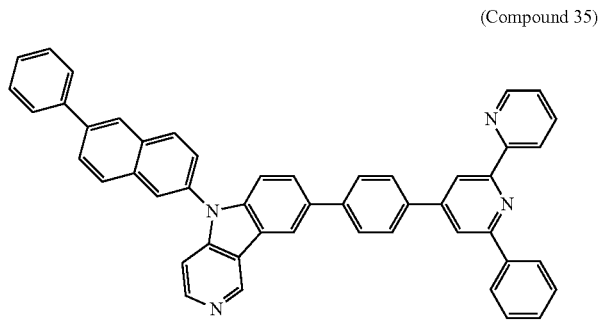
[Chemical Formula 38]
(Compound 36)
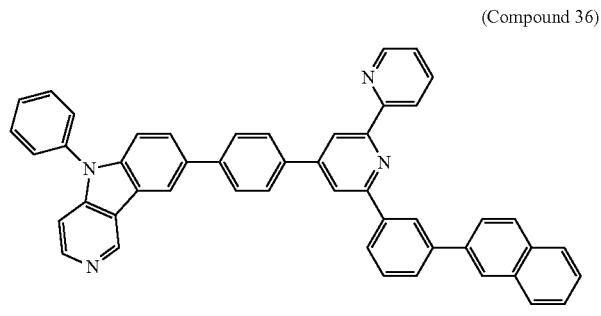

[Chemical Formula 39]
(Compound 37)
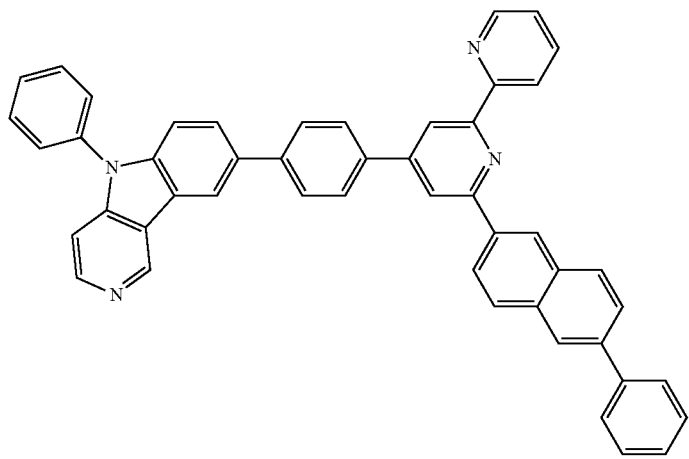
[Chemical Formula 40]
(Compound 38)
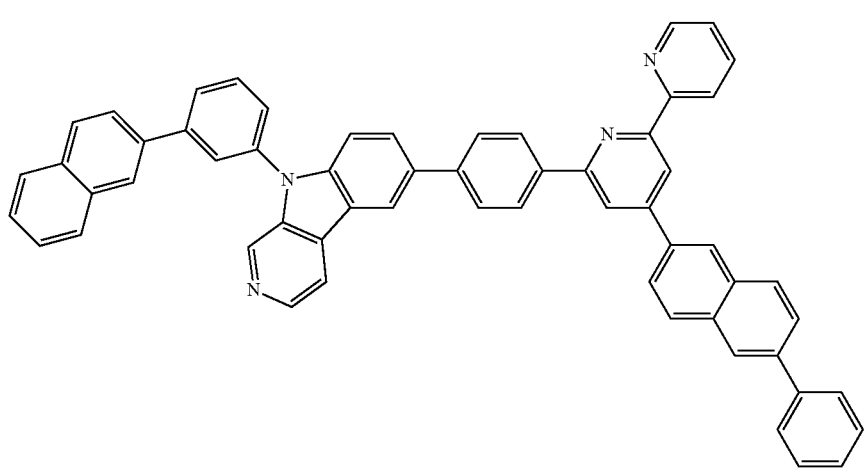
[Chemical Formula 41]
(Compound 39)
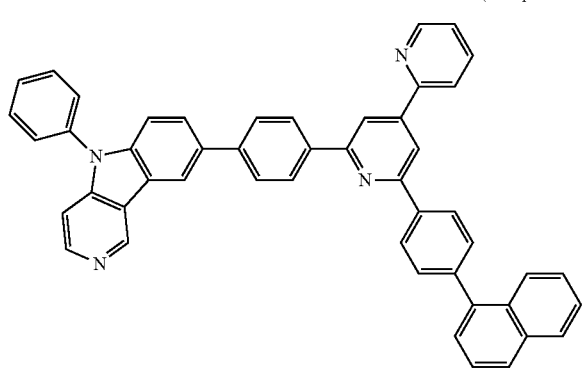
[Chemical Formula 42]
(Compound 40)
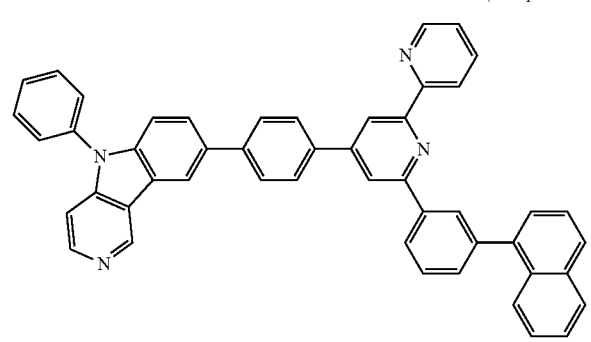

[Chemical Formula 43]
(Compound 41)
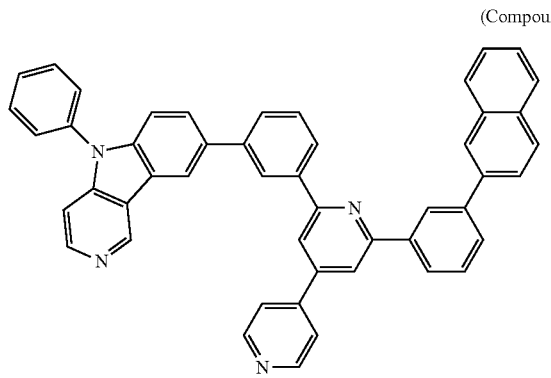
[Chemical Formula 44]
(Compound 42)
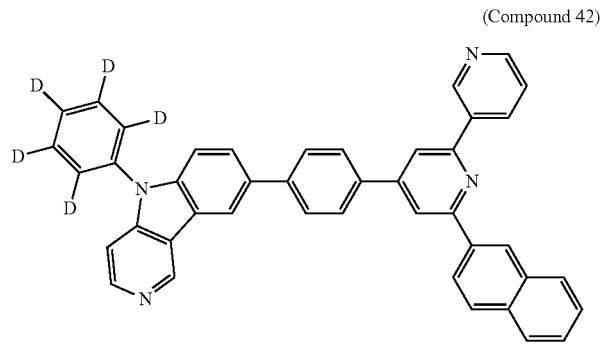
[Chemical Formula 45]
(Compound 43)
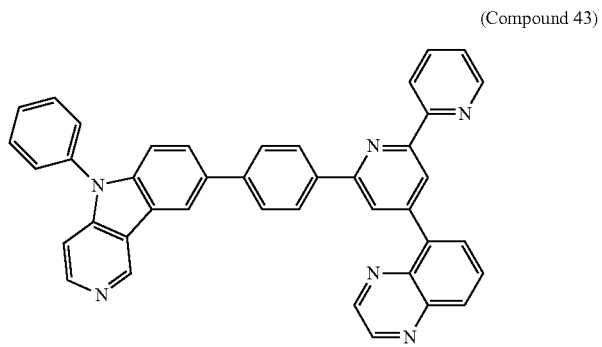
[Chemical Formula 46]
(Compound 44)
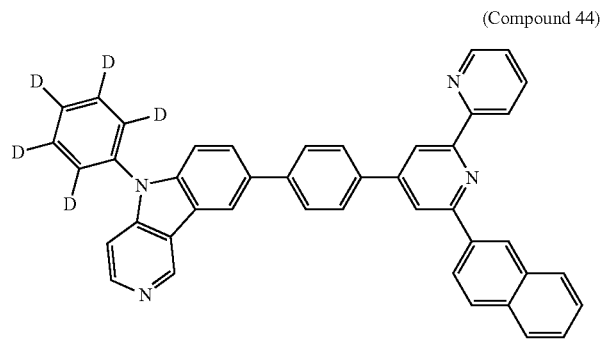
[Chemical Formula 47]
(Compound 45)
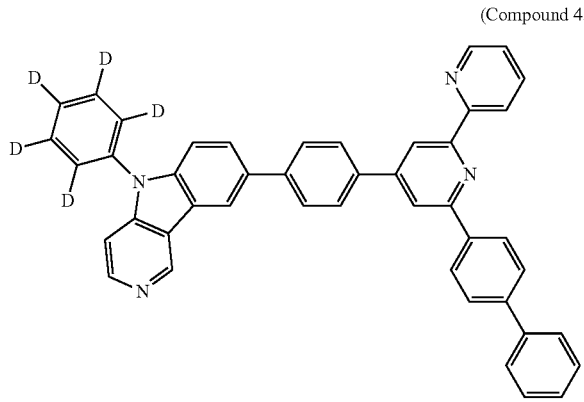
[Chemical Formula 48]
(Compound 46)
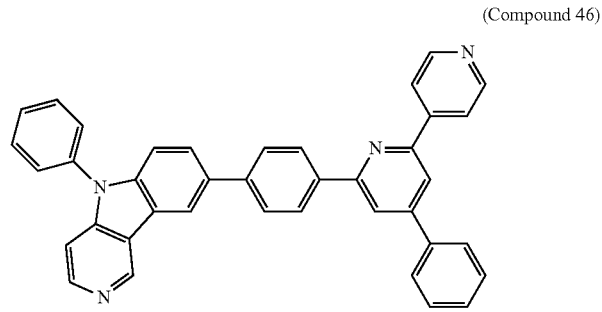

[Chemical Formula 49]
(Compound 47)
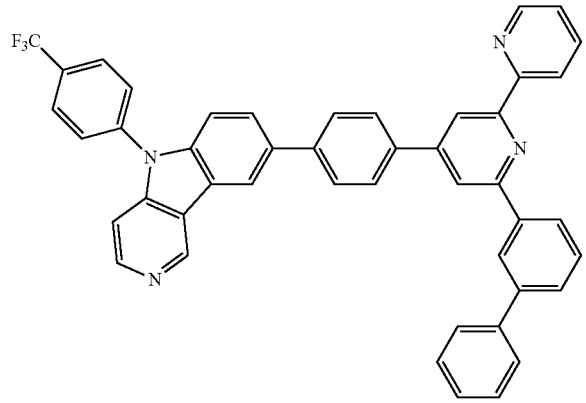
[Chemical Formula 50]
(Compound 48)
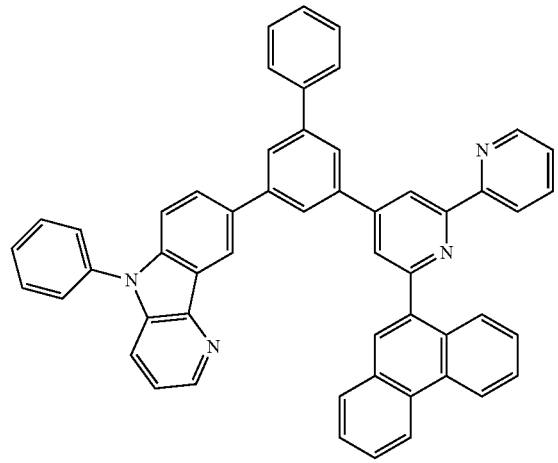
[Chemical Formula 51]
(Compound 49)
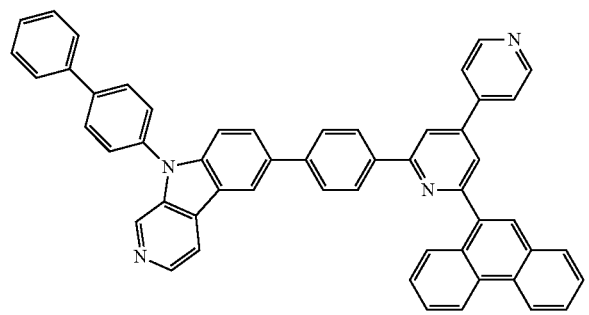
[Chemical Formula 52]
(Compound 50)
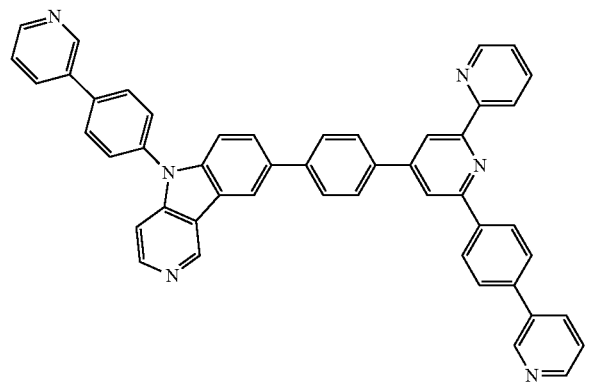
[Chemical Formula 53]
(Compound 51)
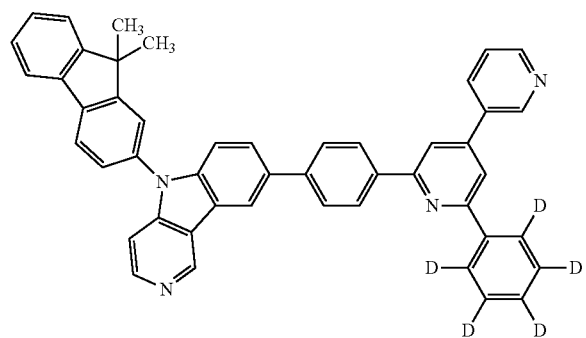
[Chemical Formula 54]
(Compound 52)
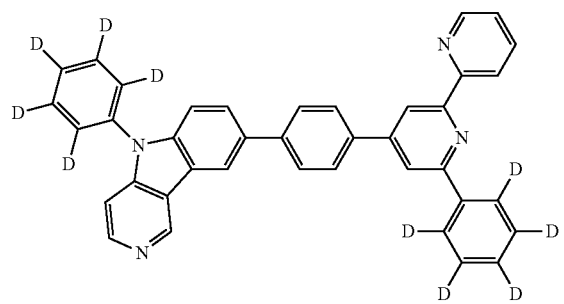

-continued
[Chemical Formula 55]
(Compound 53)
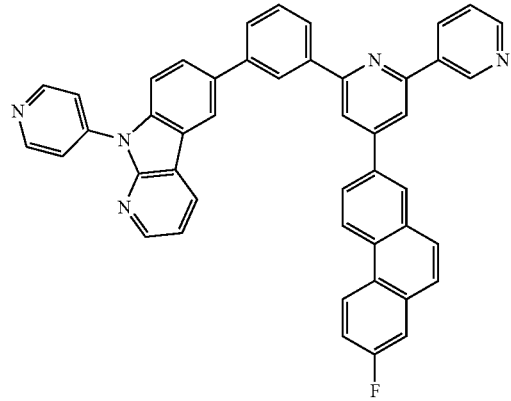
[Chemical Formula 56]
(Compound 54)
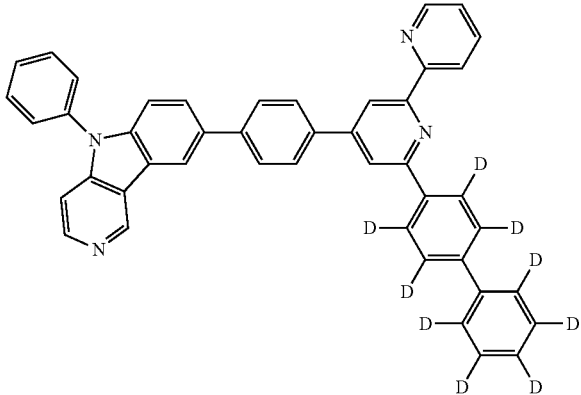
[Chemical Formula 57]
(Compound 55)
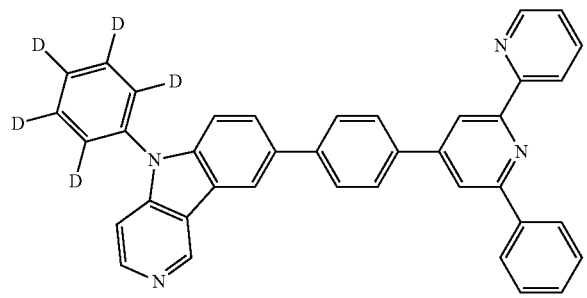
[Chemical Formula 58]
(Compound 56)
[Chemical Formula 59]
(Compound 57)
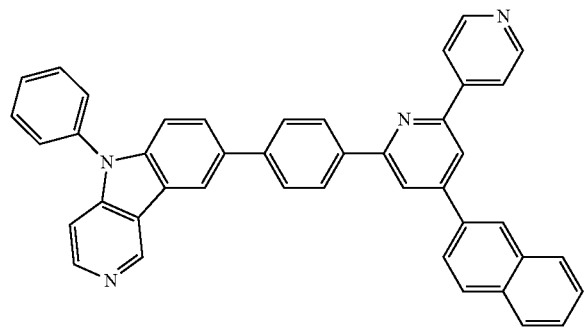
[Chemical Formula 60]
(Compound 58)
[Chemical Formula 61]
(Compoiund 59)
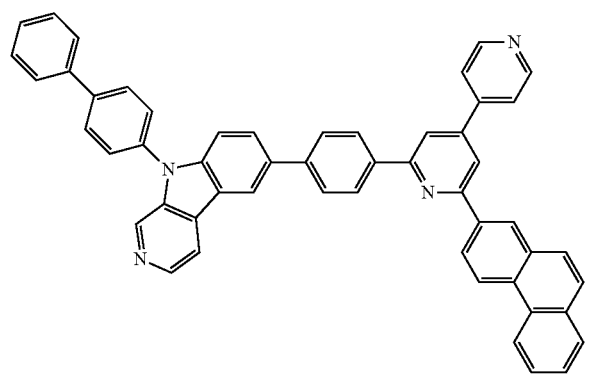
[Chemical Formula 62]
(Compound 60)
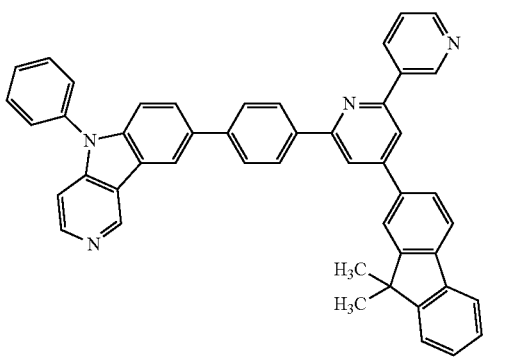

-continued
[Chemical Formula 63]
(Compound 61)
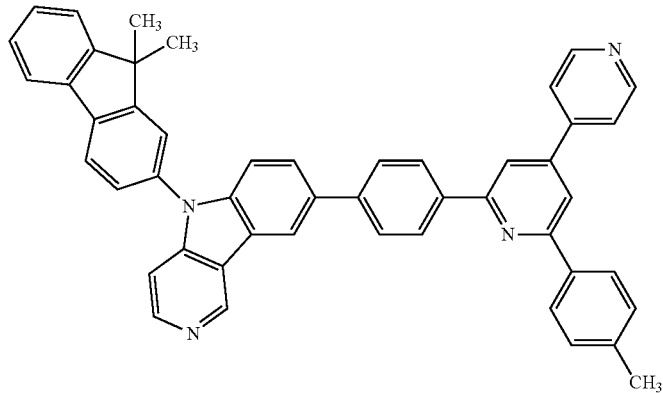
[Chemical Formula 64]
(Compound 62)
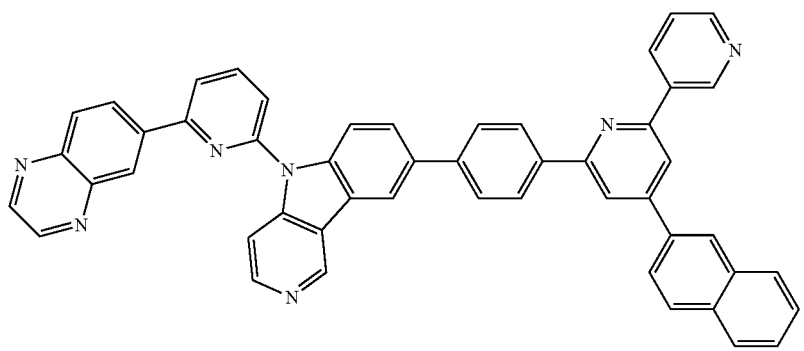
[Chemical Formula 65]
(Compound 63)
[Chemical Formula 66]
(Compound 64)
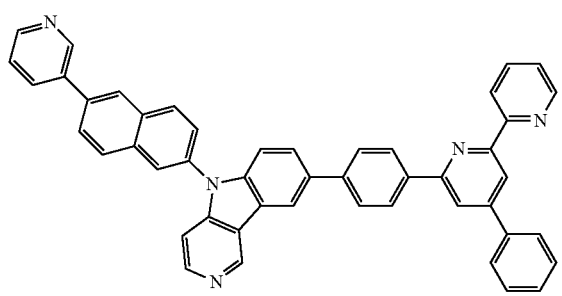

-continued
[Chemical Formula 67]
(Compound 65)
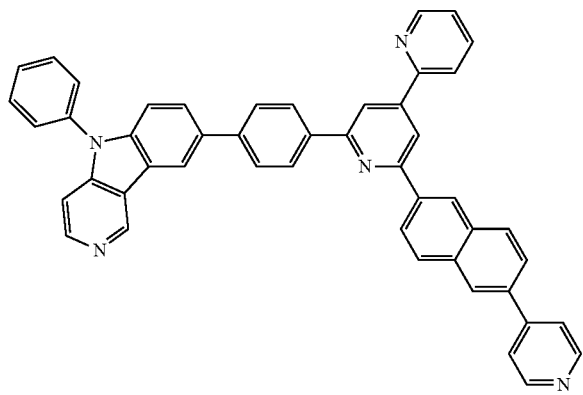
[Chemical Formula 68]
(Compound 66)
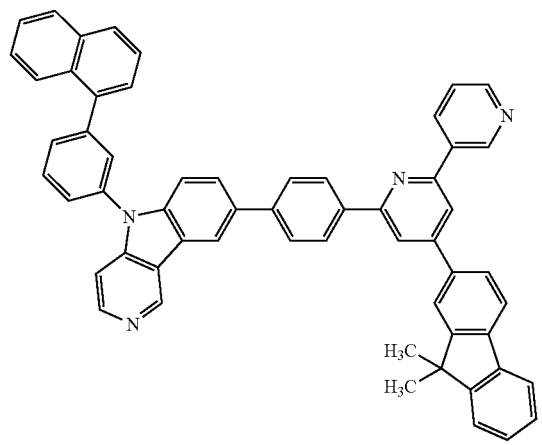
[Chemical Formula 69]
(Compound 67)
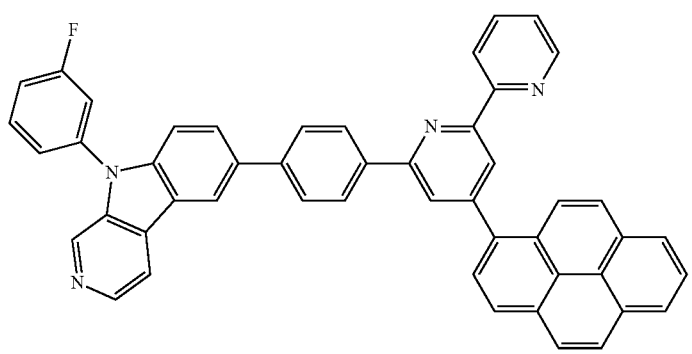
[Chemical Formula 70]
(Compound 68)
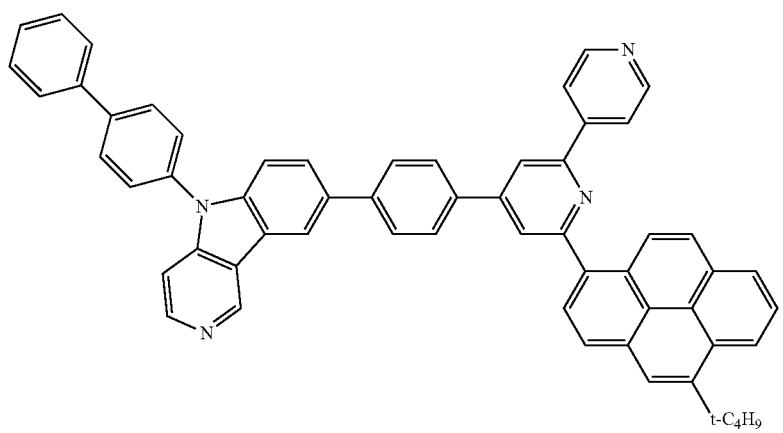

[Chemical Formula 71]
(Compound 69)
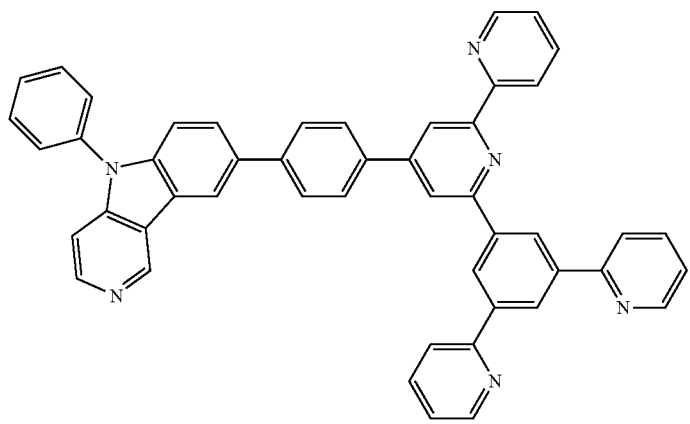
[Chemical Formula 72]
(Compound 70)
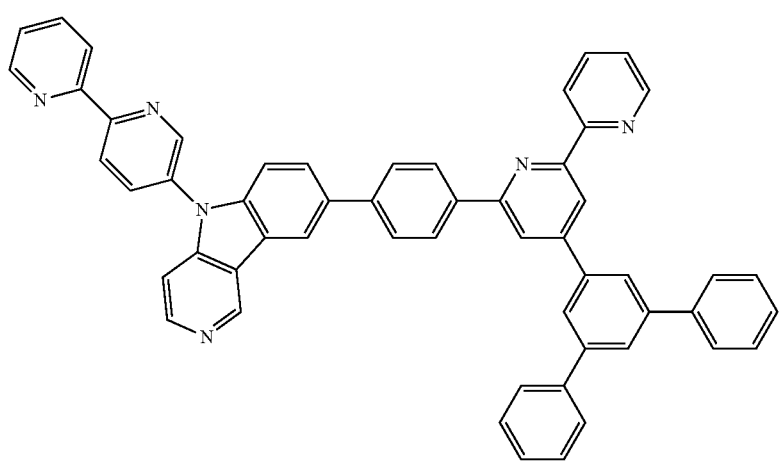
[Chemical Formula 73]
(Compound 71)
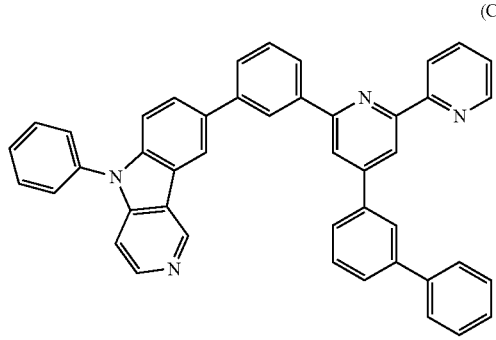
[Chemical Formula 74]
(Compound 72)
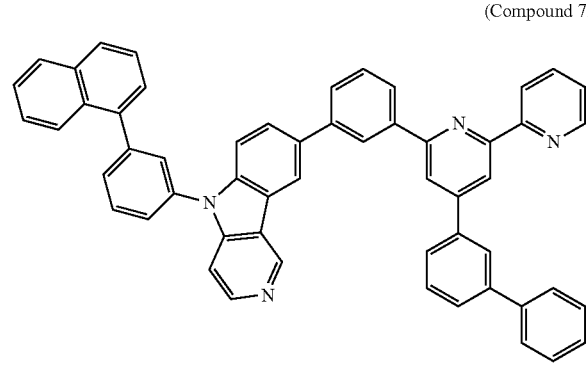

-continued
[Chemical Formula 75]
(Compound 73)
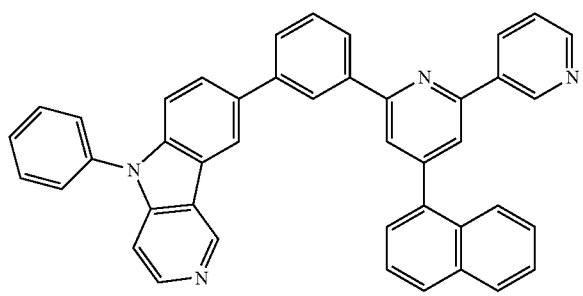
[Chemical Formula 76]
(Compound 74)
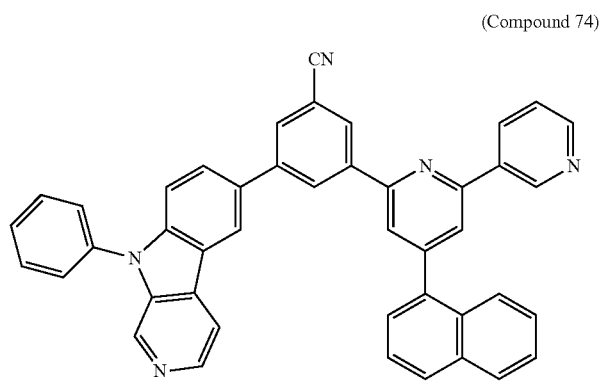
[Chemical Formula 77]
(Compound 75)
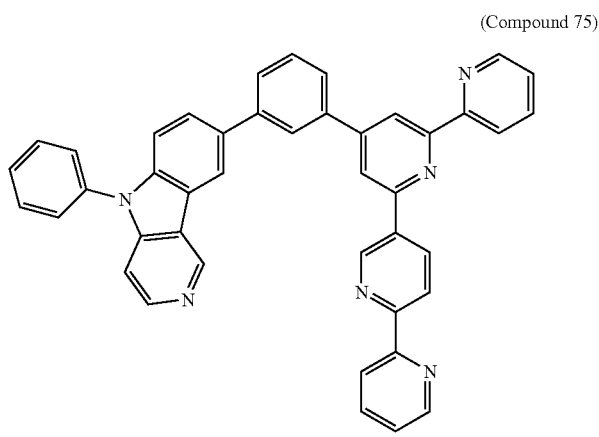
[Chemical Formula 78]
(Compound 76)
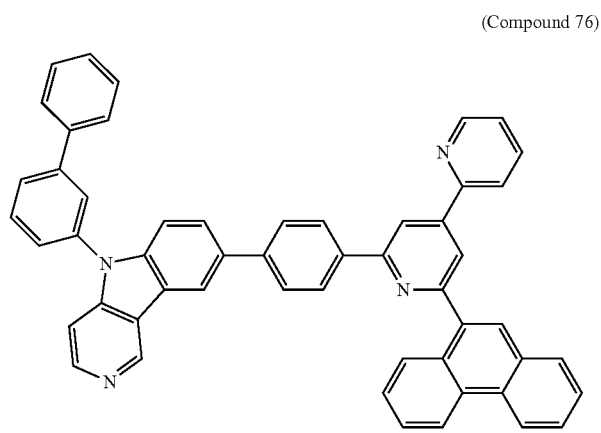
[Chemical Formula 79]
(Compound 77)
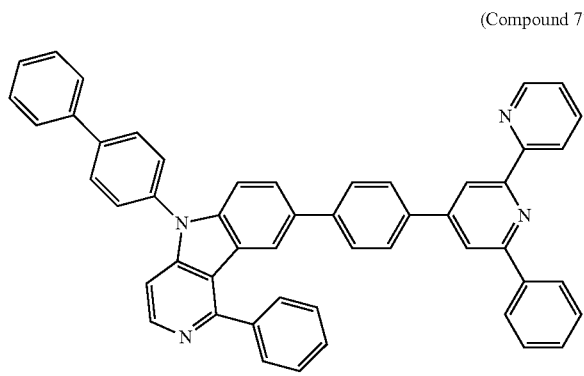
[Chemical Formula 80]
(Compound 78)
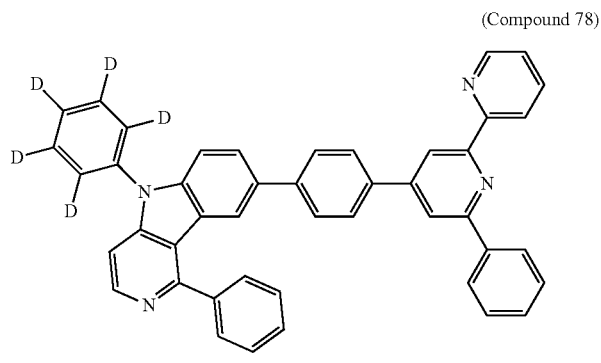
[Chemical Formula 81]
(Compound 79)
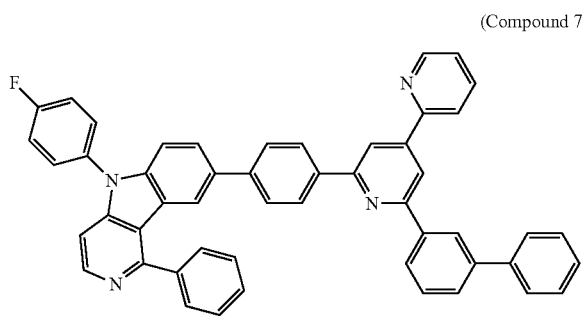
[Chemical Formula 82]
(Compound 80)
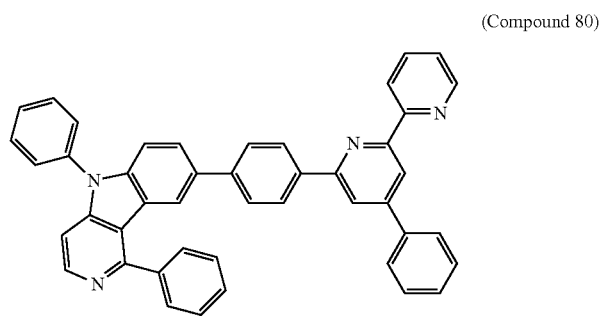

-continued
[Chemical Formula 83]
(Compound 81)
[Chemical Formula 84]
(Compound 82)
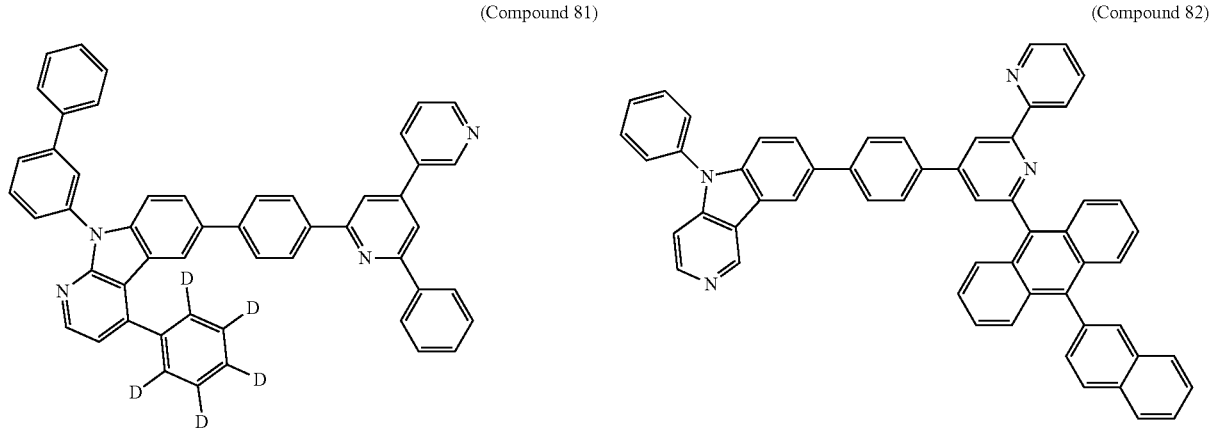
[Chemical Formula 85]
(Compound 83)
[Chemical Formula 86]
(Compound 84)
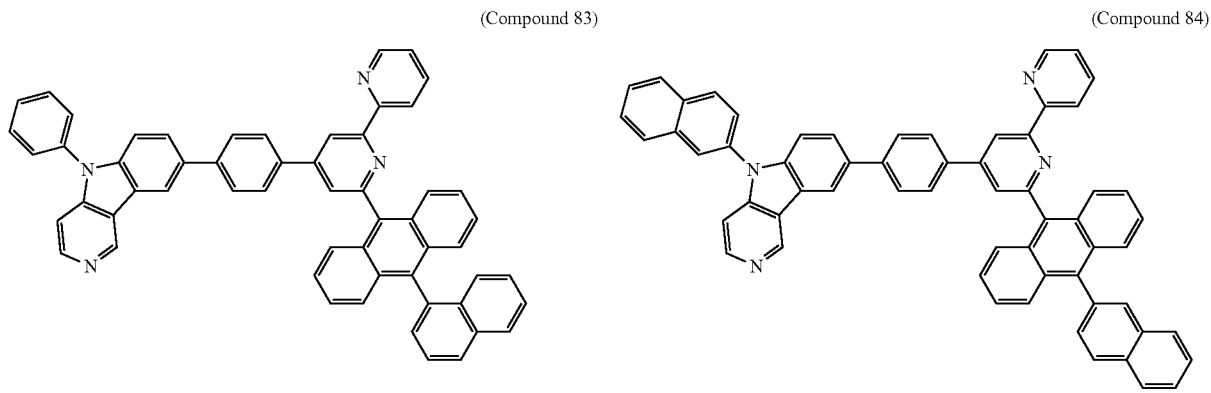
[Chemical Formula 87]
(Compound 85)
[Chemical Formula 88]
(Compound 86)
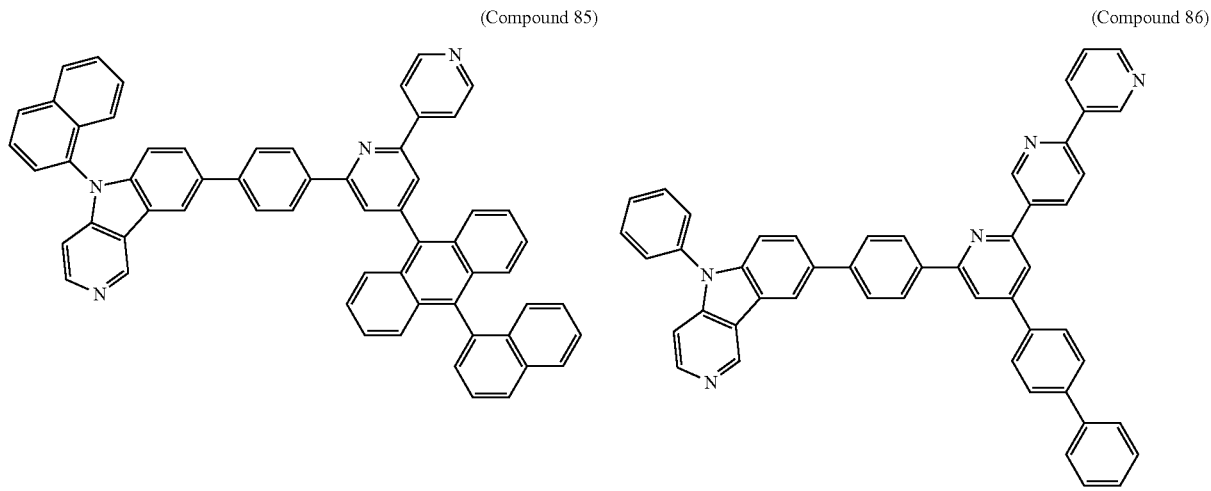

-continued
[Chemical Formula 89]
(Compound 87)
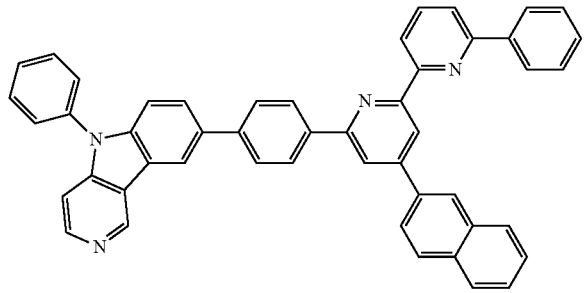
[Chemical Formula 90]
(Compound 88)
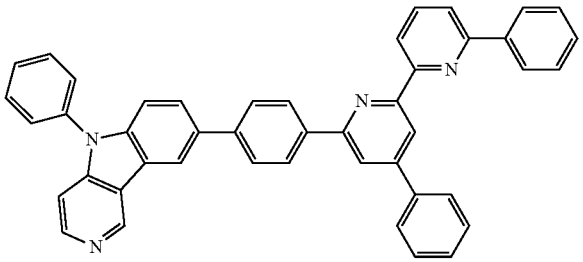
[Chemical Formula 91]
(Compound 89)
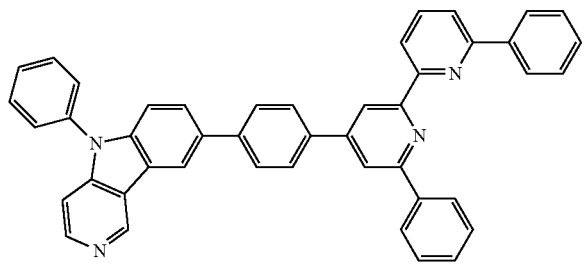
[Chemical Formula 92]
(Compound 90)
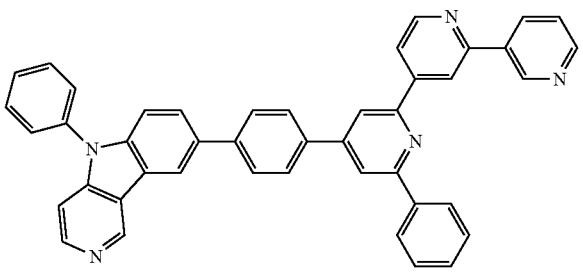
[Chemical Formula 93]
(Compound 91)
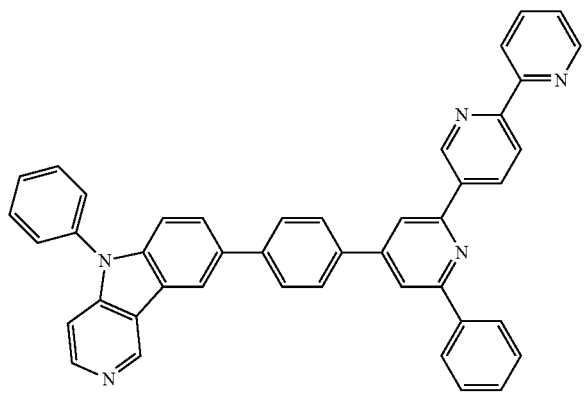
[Chemical Formula 94]
(Compound 92)
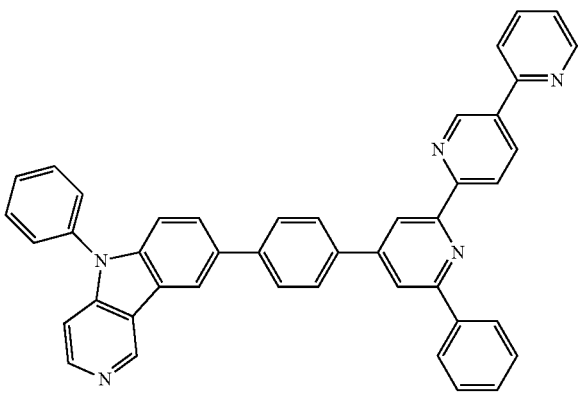

-continued
[Chemical Formula 95] (Compound 93)
[Chemical Formula 96] (Compound 94)
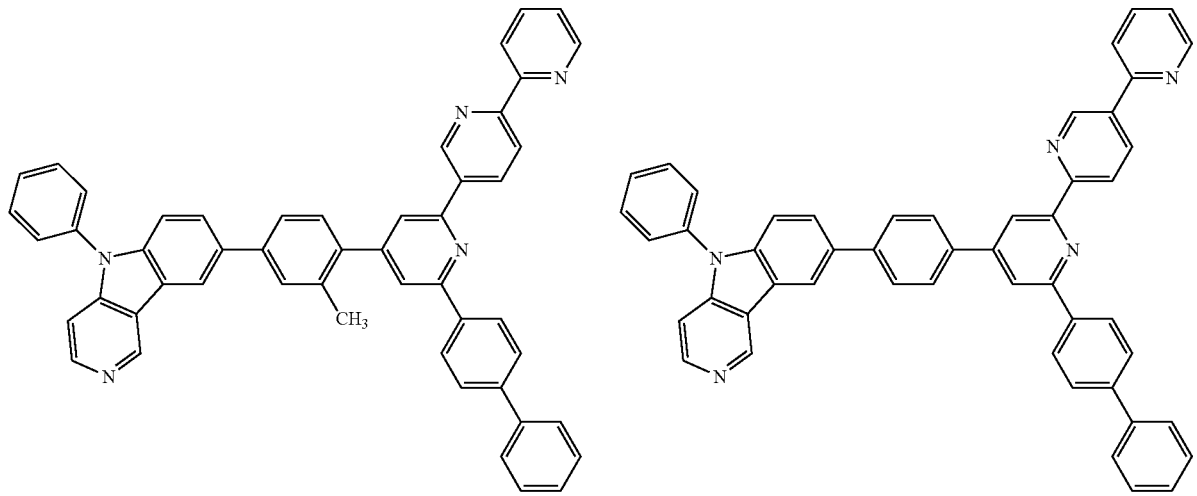
[Chemical Formula 97] (Compound 95)
[Chemical Formula 98] (Compound 96)
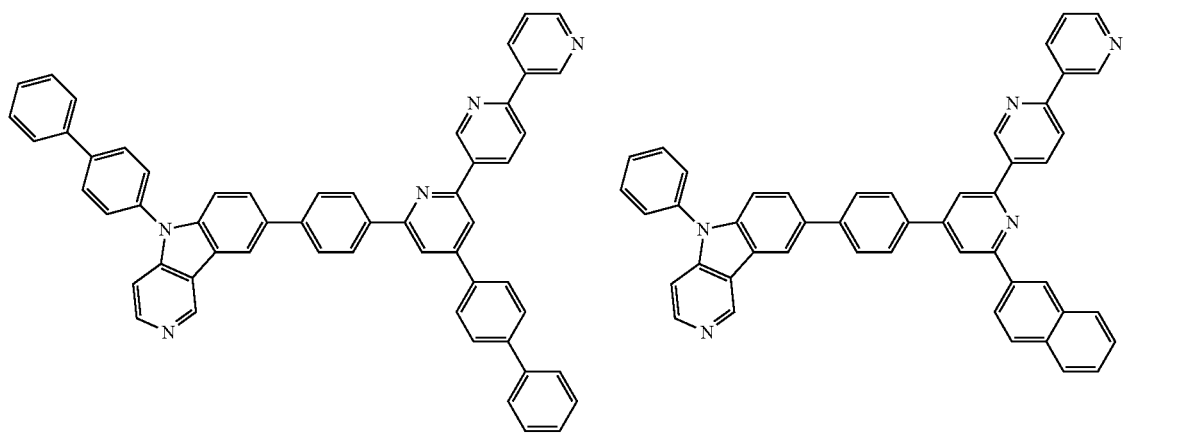
[Chemical Formula 99] (Compound 97)
[Chemical Formula 100] (Compound 98)
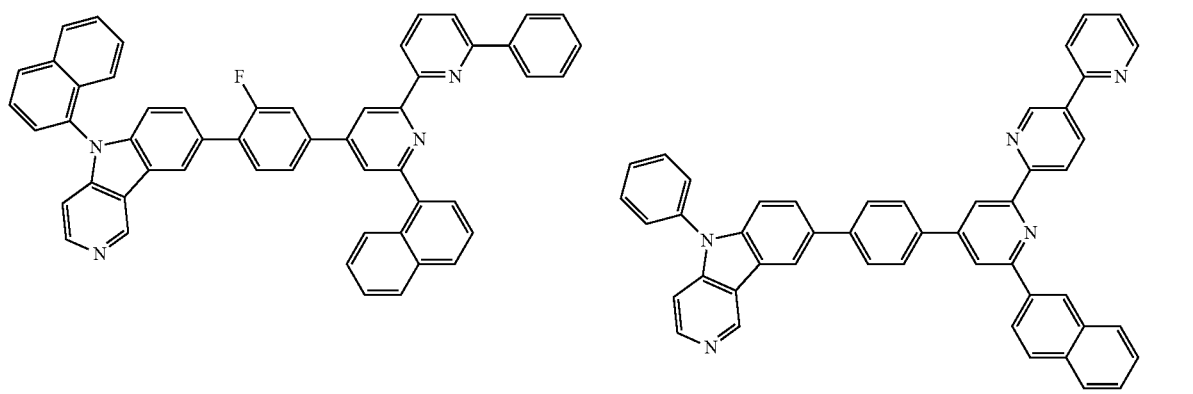

[Chemical Formula 101]

(Compound 99)

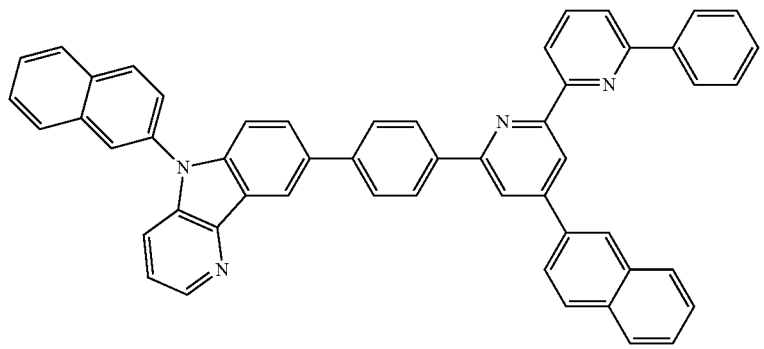

[Chemical Formula 102]

(Compound 100)

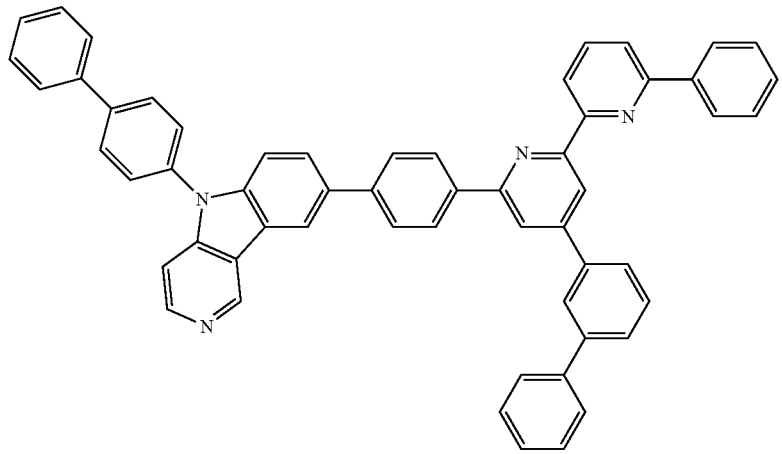

[Chemical Formula 103]

(Compound 101)

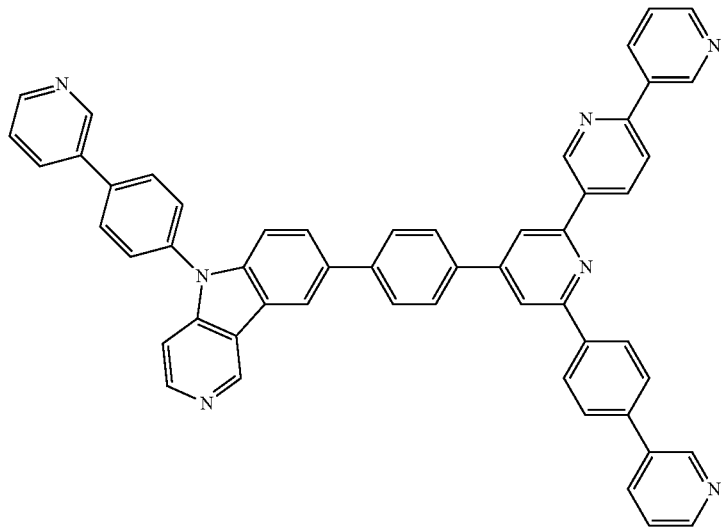

These compounds were purified by methods such as column chromatography, adsorption using, for example, silica gel, activated carbon, or activated clay, and recrystallization or crystallization using a solvent. The compounds were identified by an NMR analysis. A melting point, a glass transition point (Tg), and a work function were measured as material property values. The melting point can be used as an index of vapor deposition, the glass transition point (Tg) as an index of stability in the thin-film state, and the work function as an index of hole blocking ability.

The melting point and the glass transition point (Tg) were measured by a high-sensitive differential scanning calorimeter (DSC3100S produced by Bruker AXS) using powder.

For the measurement of the work function, a 100 nm-thick thin film was fabricated on an ITO substrate, and an atmosphere photoelectron spectrometer (Model AC-3 produced by Riken Keiki Co., Ltd.) was used.

The organic EL device of the present invention may have a structure including an anode, a hole transport layer, a light emitting layer, a hole blocking layer, an electron transport layer, and a cathode sequentially formed on a substrate, optionally with a hole injection layer between the anode and the hole transport layer, with an electron injection layer between the electron transport layer and the cathode, or with an electron blocking layer between the light emitting layer and the hole transport layer. In such multilayer structures, some of the organic layers may be omitted. For example, the device may be configured to include an anode, a hole transport layer, a light emitting layer, an electron transport layer, and a cathode sequentially formed on a substrate.

Each of the light emitting layer, the hole transport layer, and the electron transport layer may have a laminate structure of two or more layers.

Electrode materials with a large work function, such as ITO and gold, are used as the anode of the organic EL device of the present invention. The hole injection layer of the organic EL device of the present invention may be made of a material, the examples of which include starburst-type triphenylamine derivatives, triphenylamine trimers and tetramers such as an arylamine compound of a structure in which three or more triphenylamine structures are joined to each other within the molecule via a single bond or a divalent group that does not contain a heteroatom, accepting heterocyclic compounds such as hexacyano azatriphenylene, and coating-type polymer materials, in addition to porphyrin compounds as represented by copper phthalocyanine. These materials may be formed into a thin film by using a vapor deposition method, or other known methods such as a spin coating method and an inkjet method.

Examples of material used for the hole transport layer of the organic EL device of the present invention can be benzidine derivatives such as N,N'-diphenyl-N,N'-di(m-tolyl)-benzidine (hereinafter referred to as TPD), N,N'-diphenyl-N,N'-di(α-naphthyl)-benzidine (hereinafter referred to as NPD), and N,N,N',N'-tetrabiphenylylbenzidine; 1,1-bis[4-(di-4-tolylamino)phenyl]cyclohexane (hereinafter referred to as TAPC); and various triphenylamine trimers and tetramers. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. Examples of material used for the hole injection/transport layer can be coating-type polymer materials such as poly(3,4-ethylenedioxythiophene) (hereinafter referred to as PEDOT)/poly(styrene sulfonate) (hereinafter referred to as PSS). These materials may be formed into a thin-film by a vapor deposition method or other known methods such as a spin coating method and an inkjet method.

Further, material used for the hole injection layer or the hole transport layer may be obtained by p-doping trisbromophenylamine hexachloroantimony or the like into the material commonly used for these layers, or may be, for example, polymer compounds each having a TPD structure as a part of the compound structure.

Examples of material used for the electron blocking layer of the organic EL device of the present invention can be compounds having an electron blocking effect, including, for example, carbazole derivatives such as 4,4',4''-tri(N-carbazolyl)triphenylamine (hereinafter referred to as TCTA), 9,9-bis[4-(carbazol-9-yl)phenyl]fluorene, 1,3-bis(carbazol-9-yl)benzene (hereinafter referred to as mCP), and 2,2-bis(4-carbazol-9-ylphenyl)adamantane (hereinafter referred to as Ad-Cz); and compounds having a triphenylsilyl group and a triarylamine structure, as represented by 9-[4-(carbazol-9-yl)phenyl]-9-[4-(triphenylsilyl)phenyl]-9H-fluorene. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the light emitting layer of the organic EL device of the present invention can be various metal complexes, anthracene derivatives, bis(styryl)benzene derivatives, pyrene derivatives, oxazole derivatives, and polyparaphenylene vinylene derivatives, in addition to quinolinol derivative metal complexes such as $Alq_3$, and the compounds of the present invention in which a substituted bipyridyl group and a pyridoindole ring structure are bonded via a phenylene group. Further, the light emitting layer may comprise a host material and a dopant material. Examples of the host material can be thiazole derivatives, benzimidazole derivatives, and polydialkyl fluorene derivatives in addition to the above light-emitting materials. Examples of the dopant material can be quinacridone, coumarin, rubrene, perylene, derivatives thereof, benzopyran derivatives, rhodamine derivatives, and aminostyryl derivatives. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer.

A phosphorescent light-emitting material may be used as the light-emitting material. Phosphorescent materials as metal complexes of metals such as iridium and platinum may be used as the phosphorescent light-emitting material. Examples of the phosphorescent materials include green phosphorescent materials such as $Ir(ppy)_3$, blue phosphorescent materials such as FIrpic and $FIr_6$, and red phosphorescent materials such as $Btp_2Ir(acac)$. Carbazole derivatives such as 4,4'-di(N-carbazolyl)biphenyl (hereinafter referred to as CBP), TCTA, and mCP may be used as the hole injecting and transporting host material. Compounds such as p-bis(triphenylsilyl)benzene (hereinafter referred to as UGH2), and 2,2',2''-(1,3,5-phenylene)-tris(1-phenyl-1H-benzimidazole) (hereinafter referred to as TPBI) may be used as the electron transporting host material.

In order to avoid concentration quenching, the doping of the host material with the phosphorescent light-emitting material should preferably be made by co-evaporation in a range of 1 to 30 weight percent with respect to the whole light emitting layer.

These materials may be formed into a thin-film by using a vapor deposition method, or other known methods such as a spin coating method and an inkjet method.

The hole blocking layer of the organic EL device of the present invention may be formed by using hole blocking compounds such as various rare earth complexes, oxazole derivatives, triazole derivatives, and triazine derivatives, in addition to the metal complexes of phenanthroline derivatives such as bathocuproin (hereinafter referred to as BCP), the metal complexes of quinolinol derivatives such as BAlq, and the compounds of the present invention in which a substituted bipyridyl group and a pyridoindole ring structure are bonded via a phenylene group. These materials may also serve as the material of the electron transport layer. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method, or other known methods such as a spin coating method and an inkjet method.

Examples of the material used for the electron transport layer of the organic EL device of the present invention include various metal complexes, triazole derivatives, triazine derivatives, oxadiazole derivatives, thiadiazole derivatives, carbodiimide derivatives, quinoxaline derivatives, phenanthroline derivatives, and silole derivatives, in addition to quinolinol derivative metal complexes such as $Alq_3$ and BAlq, and the compounds of the present invention in which a substituted bipyridyl group and a pyridoindole ring structure are bonded via a phenylene group. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method, or other known methods such as a spin coating method and an inkjet method.

Examples of the material used for the electron injection layer of the organic EL device of the present invention include alkali metal salts (such as lithium fluoride, and cesium fluoride), alkaline earth metal salts (such as magnesium fluoride), and metal oxides (such as aluminum oxide), in addition to the compounds of the present invention in which a substituted bipyridyl group and a pyridoindole ring structure are bonded via a phenylene group. However, the electron injection layer may be omitted upon preferably selecting the electron transport layer and the cathode.

The electron injection layer or the electron transport layer may be one obtained by the N-doping of metals such as cesium in the materials commonly used for these layers.

The cathode of the organic EL device of the present invention may be made of an electrode material having a low work function (such as aluminum), or an alloy of an electrode material having an even lower work function (such as a magnesium-silver alloy, a magnesium-indium alloy, or an aluminum-magnesium alloy).

The following describes embodiments of the present invention more specifically based on Examples. The present invention, however, is not restricted to the following Examples.

EXAMPLE 1

Synthesis of 8-[4-{6-(naphthalen-2-yl)-[2,2']bipyridine-4-yl}-phenyl]-5-phenyl-5H-pyrido[4,3-b]indole (Compound 2)

2'-Acetonaphthone (16.1 g), iodine (24.2 g), and pyridine (72 ml) were added into a reaction vessel, heated, and stirred at 100° C. for 3 hours. The mixture was cooled to a room temperature, and after water (170 ml) was added, purification by recrystallization was performed. The product was dried under reduced pressure at 70° C. for 12 hours to obtain a brown powder of 1-{2-(naphthalen-2-yl)-2-oxoethyl}pyridinium iodide (31.3 g; yield 88%).

4-Bromobenzaldehyde (15.4 g), 2-acetylpyridine (10.1 g) and methanol (140 ml) were added beforehand into a reaction vessel and cooled to –5° C. while being stirred, and then a 3% (wt/wt) NaOH methanol solution (140 ml) was dropped and further stirred for 2 days to prepare a solution. The obtained 1-{2-(naphthalen-2-yl)-2-oxoethyl}pyridinium iodide (31.3 g), ammonium acetate (80.3 g) and methanol (180 ml) were added to the prepared solution, heated and stirred at 55° C. for 2 days. The mixture was cooled to a room temperature, and a deposited crude product was collected by filtration, washed with methanol, and dried under reduced pressure at 70° C. for 12 hours to obtain a grey powder of 4-(4-bromophenyl)-6-(naphthalen-2-yl)-[2,2']bipyridine (14.3 g; yield 39%).

The obtained 4-(4-bromophenyl)-6-(naphthalen-2-yl)-[2,2']bipyridine (3.6 g), 8-bromo-5-phenyl-5H-pyrido[4,3-b]indole (3.7 g), tetrakis(triphenylphosphine)palladium (0) (0.3 g), a 2M potassium carbonate solution (12.5 ml), toluene (30 ml), and ethanol (7 ml) were added into a reaction vessel substituted with nitrogen, and heated under reflux for 3 hours while being stirred. The mixture was cooled to a room temperature, and a deposited crude product was collected by filtration. The crude product was purified by column chromatography (carrier: NH silica gel, and eluent: toluene) to obtain a white powder of 8-[4-{6-(naphthalen-2-yl)-[2,2']bipyridine-4-yl}-phenyl]-5-phenyl-5H-pyrido[4,3-b]indole (Compound 2) (3.1 g; yield 61%).

The structure of the resulting white powder was identified by NMR. The $^1$H-NMR measurement result is presented in FIG. 1.

$^1$H-NMR (CDCl$_3$) detected 28 hydrogen signals, as follows. δ (ppm)=9.48 (1H), 8.75-8.80 (3H), 8.69 (1H), 8.56 (1H), 8.51 (1H), 8.41 (1H), 8.22 (1H), 8.00-8.05 (4H), 7.88-7.95 (4H), 7.81 (1H), 7.67 (2H), 7.52-7.62 (6H), 7.38 (1H), 7.33 (1H).

EXAMPLE 2

Synthesis of 8-[4-{6-(biphenyl-4-yl)-[2,2']bipyridinyl-4-yl}-phenyl]-5-phenyl-5H-pyrido[4,3-b]indole (Compound 8)

The same process as Example 1 was applied to synthesize 6-(biphenyl-4-yl)-4-(4-bromophenyl)-[2,2']bipyridine from 4-acetylbiphenyl. The obtained 6-(biphenyl-4-yl)-4-(4-bromophenyl)-[2,2']bipyridine (3.7 g), 8-bromo-5-phenyl-5H-pyrido[4,3-b]indole (3.3 g), tetrakis(triphenylphosphine)palladium (0) (0.3 g), a 2M potassium carbonate solution (12 ml), toluene (30 ml), and ethanol (7 ml) were added into a reaction vessel substituted with nitrogen, and heated under reflux for 3 hours while being stirred. The mixture was cooled to a room temperature, and a deposited crude product was collected by filtration. The crude product was purified by column chromatography (carrier: NH silica gel, and eluent: toluene) to obtain a white powder of 8-[4-{6-(biphenyl-4-yl)-[2,2']bipyridinyl-4-yl}-phenyl]-5-phenyl-5H-pyrido[4,3-b]indole (Compound 8) (1.7 g; yield 34%).

The structure of the resulting white powder was identified by NMR. The $^1$H-NMR measurement result is presented in FIG. 2.

$^1$H-NMR (CDCl$_3$) detected 30 hydrogen signals, as follows. δ (ppm)=9.49 (1H), 8.74 (3H), 8.57 (1H), 8.51 (1H), 8.33 (2H), 8.12 (1H), 8.00 (2H), 7.95-8.05 (3H), 7.80 (3H), 7.65-7.75 (4H), 7.60 (2H), 7.55 (2H), 7.50 (2H), 7.35-7.43 (2H), 7.34 (1H).

EXAMPLE 3

The melting point and glass transition point of the compounds of the present invention were determined using a high-sensitive differential scanning calorimeter (DSC 3100S produced by Bruker AXS).

|  | Melting point | Glass transition point |
| --- | --- | --- |
| Compound of Example 1 of the present invention | 255° C. | 122° C. |
| Compound of Example 2 of the present invention | 246° C. | 128° C. |

The compounds of the present invention have glass transition points of 100° C. or higher. This demonstrates that the compounds of the present invention have a stable thin-film state.

EXAMPLE 4

A 100 nm-thick vapor-deposited film was fabricated on an ITO substrate using the compounds of the present invention, and a work function was measured using an atmosphere photoelectron spectrometer (Model AC-3 produced by Riken Keiki Co., Ltd.).

|  | Work function |
| --- | --- |
| Compound of Example 1 of the present invention | 6.06 eV |
| Compound of Example 2 of the present invention | 6.15 eV |

As shown in the above, the compounds of the present invention have a greater work function value than 5.4 eV of ordinary hole-transporting materials such as NPD and TPD, and therefore have a greater hole-blocking ability.

EXAMPLE 5

An organic EL device, as shown in FIG. 3, was fabricated by forming a hole injection layer 3, a hole transport layer 4, a light emitting layer 5, a hole blocking layer 6, an electron transport layer 7, an electron injection layer 8, and a cathode (an aluminum electrode) 9 in this order by vapor deposition on a glass substrate 1 formed beforehand with an ITO electrode as a transparent anode 2.

Specifically, the glass substrate 1 having ITO (thickness 150 nm) formed thereon was washed with an organic solvent, and subjected to an oxygen plasma treatment to wash the surface. The glass substrate with the ITO electrode was then installed in a vacuum vapor deposition apparatus, and the pressure was reduced to 0.001 Pa or less. This was followed by formation of the hole injection layer 3 by forming Compound 102 of the structural formula below over the transparent anode 2 in a thickness of 20 nm at a deposition rate of 6 nm/min. The hole transport layer 4 was then formed on the hole injection layer 3 by forming Compound 103 of the structural formula below, in a thickness of 40 nm at a deposition rate of 6 nm/min. Thereafter, the light emitting layer 5 was formed on the hole transport layer 4 by forming Compounds 104 and 105 of the structural formulae below, in a thickness of 30 nm using dual vapor deposition at a deposition rate ratio of Compound 104: Compound 105=5:95. The hole blocking layer-electron transport layer 6 and 7 were then formed on the light emitting layer 5 by forming the compound of Example 1 of the present invention (Compound 2) in a thickness of 30 nm at a deposition rate of 6 nm/min. Then, the electron injection layer 8 was formed on the hole blocking layer-electron transport layer 6 and 7 by forming lithium fluoride in a thickness of 0.5 nm at a deposition rate of 0.6 nm/min. Finally, the cathode 9 was formed by vapor depositing aluminum in a thickness of 150 nm. The characteristics of the organic EL device thus fabricated were measured at an ordinary temperature in the atmosphere.

Table 1 summarizes the results of the emission characteristics measurements performed by applying a DC voltage to the organic EL device fabricated with the compound of Example 1 of the present invention (Compound 2).

[Chemical Formula 104]

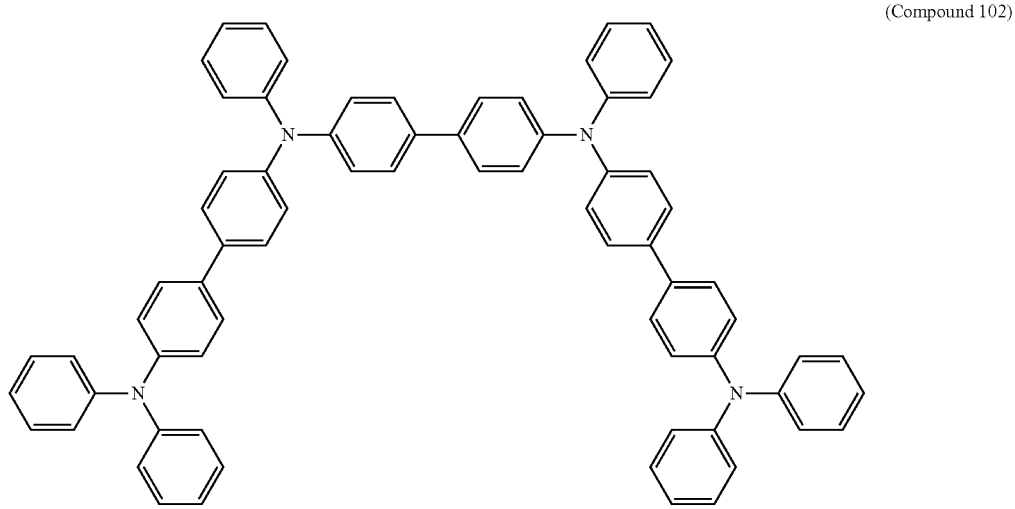

(Compound 102)

[Chemical Formula 105]

(Compound 103)

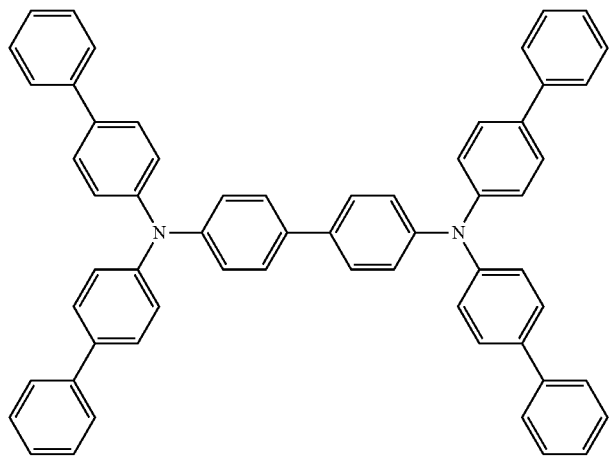

[Chemical Formula 106]

(Compound 104)

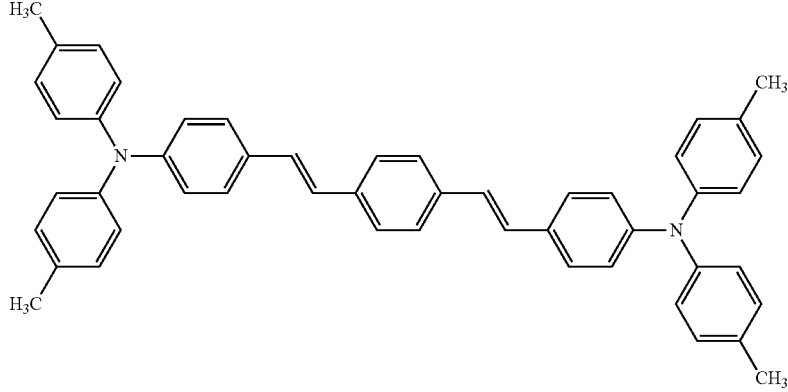

[Chemical Formula 107]

(Compound 105)

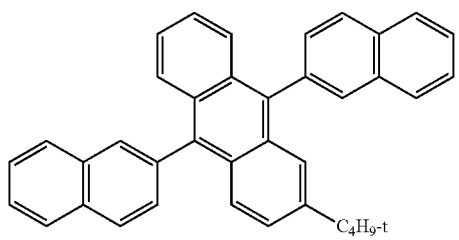

EXAMPLE 6

An organic EL device was fabricated under the same conditions used in Example 5, except that the compound of Example 2 of the present invention (Compound 8) was used as the material of the hole blocking layer-electron transport layer 6 and 7 in Example 5 instead of the compound of Example 1 of the present invention (Compound 2). The characteristics of the organic EL device thus fabricated were measured at an ordinary temperature in the atmosphere.

Table 1 summarizes the results of the emission characteristics measurements performed by applying a DC voltage to the organic EL device thus fabricated.

COMPARATIVE EXAMPLE 1

For comparison, an organic EL device was fabricated under the same conditions used in Example 5, except that Compound 106 of the structural formula below (refer to Patent Document 4, for example) was used as the material of the electron transport layer 7, instead of forming the hole blocking layer-electron transport layer 6 and 7. The characteristics of the organic EL device thus fabricated were measured at an ordinary temperature in the atmosphere.

Table 1 summarizes the results of the emission characteristics measurements performed by applying a DC voltage to the organic EL device thus fabricated.

[Chemical Formula 108]

(Compound 106)

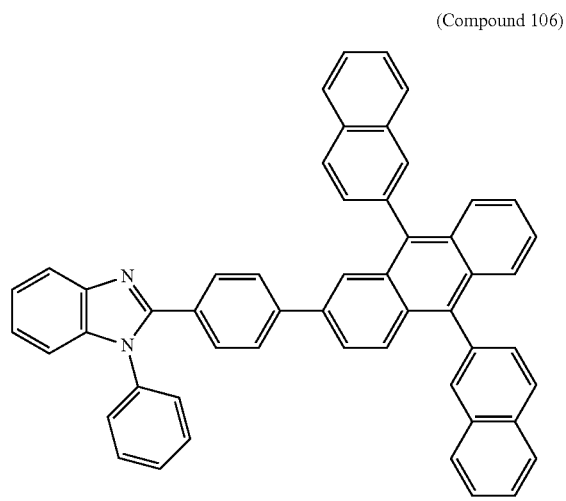

TABLE 1

| Compound | | Voltage [V] (@ 10 mA/cm$^2$) | Luminance [cd/m$^2$] (@ 10 mA/cm$^2$) | Current efficiency [cd/A] (@ 10 mA/cm$^2$) | Power efficiency [lm/W] (@ 10 mA/cm$^2$) |
|---|---|---|---|---|---|
| Example 5 | Compound 2 | 4.33 | 1034 | 10.34 | 7.51 |
| Example 6 | Compound 8 | 5.24 | 871 | 8.71 | 5.23 |
| Comparative Example 1 | Compound 106 | 5.95 | 792 | 7.92 | 4.19 |

As shown in Table 1, the driving voltage at the current density of 10 mA/cm$^2$ was as low as 4.33 V in Example 5 and 5.24 V in Example 6, compared with 5.95 V in Comparative Example 1 using Compound 106 of the structural formula, and furthermore, there were great improvements in luminance, luminous efficiency, and power efficiency measured at the current density of 10 mA/cm$^2$.

The measurement results of turn on voltage are as follows.

| Organic EL device | Compound | Turn on voltage [V] |
|---|---|---|
| Example 5 | Compound 2 | 2.7 |
| Example 6 | Compound 8 | 2.9 |
| Comparative Example 1 | Compound 106 | 3.1 |

It can be seen that the turn on voltage was lower in Examples 5 and 6 than in Comparative Example 1 that used Compound 106 of the structural formula.

It was therefore found that the organic EL device of the present invention had superior luminous efficiency and power efficiency compared with the devices that used Compound 106 of the structural formula which is the common electron transport material, and could remarkably lower the actual driving voltage.

INDUSTRIAL APPLICABILITY

The compound of the present invention in which a substituted bipyridyl group and a pyridoindole ring structure are bonded via a phenylene group, has good electron injection characteristics, excels in hole blocking ability, and thus has a stable thin-film state. The compound is therefore excellent as a compound for organic EL devices. The organic EL device fabricated with the compound can have high efficiency, a low driving voltage, and improved durability. There are potential applications for, for example, home electronic appliances and illuminations.

DESCRIPTION OF REFERENCE NUMERAL

1 Glass substrate
2 Transparent anode
3 Hole injection layer
4 Hole transport layer
5 Light emitting layer
6 Hole blocking layer
7 Electron transport layer
8 Electron injection layer
9 Cathode

The invention claimed is:

1. A compound of the following general formula (1) in which a substituted bipyridyl group and a pyridoindole ring structure are bonded via a phenylene group,

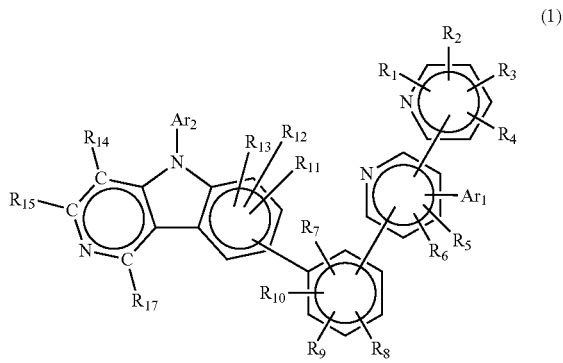

wherein Ar$_1$ represents a naphthyl group;

Ar$_2$ represents biphenyl, naphthyl-phenyl, phenyl-naphthyl, pyridyl-phenyl, pyridyl-naphthyl, bipyridyl, CF$_3$-subsituted phenyl, F-substituted phenyl or an unsubstituted condensed polycyclic aromatic group;

and R$_1$ to R$_{15}$ and R$_{17}$ may be the same or different, and represent a hydrogen atom, a deuterium atom, a fluorine atom, a chlorine atom, a cyano group, a trifluoromethyl group, or a linear or branched alkyl group of 1 to 6 carbon atoms.

2. The compound in which a substituted bipyridyl group and a pyridoindole ring structure are bonded via a phenylene group according to claim 1, wherein the compound is represented by the following general formula (1'),

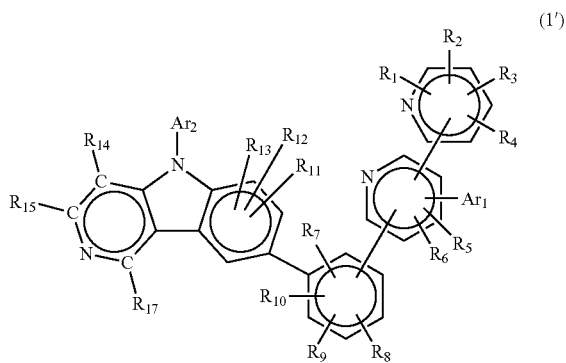

(1')

wherein Ar₁ represents a naphthyl group;

Ar₂ represents biphenyl, naphthyl-phenyl, phenyl-naphthyl, pyridyl-phenyl, pyridyl-naphthyl, bipyridyl, CF₃-susbituted phenyl, F-substituted phenyl or an unsubstituted condensed polycyclic aromatic group;

and R₁ to R₁₅ and R₁₇ may be the same or different, and represent a hydrogen atom, a deuterium atom, a fluorine atom, a chlorine atom, a cyano group, a trifluoromethyl group, or a linear or branched alkyl group of 1 to 6 carbon atoms.

3. The compound in which a substituted bipyridyl group and a pyridoindole ring structure are bonded via a phenylene group according to claim 1, wherein the compound is represented by the following general formula (1″),

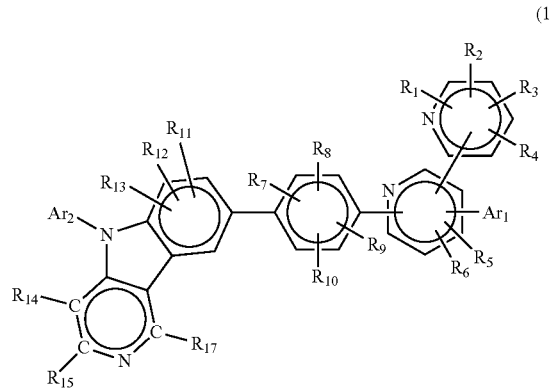

(1″)

wherein Ar₁ represents a naphthyl group;

Ar₂ represents biphenyl, naphthyl-phenyl, phenyl-naphthyl, pyridyl-phenyl, pyridyl-naphthyl, bipyridyl, CF₃-susbituted phenyl, F-substituted phenyl or an unsubstituted condensed polycyclic aromatic group;

and R₁ to R₁₅ and R₁₇ may be the same or different, and represent a hydrogen atom, a deuterium atom, a fluorine atom, a chlorine atom, a cyano group, a trifluoromethyl group, or a linear or branched alkyl group of 1 to 6 carbon atoms.

4. An organic electroluminescent device that comprises a pair of electrodes, and one or more organic layers sandwiched between the pair of electrodes, wherein a compound of the following general formula (1) in which a substituted bipyridyl group and a pyridoindole ring structure are bonded via a phenylene group, is used as a constituent material of at least one organic layer,

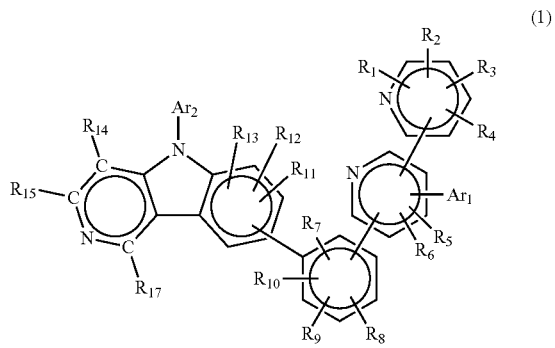

(1)

wherein Ar₁ represents a naphthyl group;

Ar₂ represents biphenyl, naphthyl-phenyl, phenyl-naphthyl, pyridyl-phenyl, pyridyl-naphthyl, bipyridyl, CF₃-susbituted phenyl, F-substituted phenyl or an unsubstituted condensed polycyclic aromatic group;

and R₁ to R₁₅ and R₁₇ may be the same or different, and represent a hydrogen atom, a deuterium atom, a fluorine atom, a chlorine atom, a cyano group, a trifluoromethyl group, or a linear or branched alkyl group of 1 to 6 carbon atoms.

5. The organic electroluminescent device according to claim 4, wherein the organic layer is an electron transport layer, and the compound represented by the general formula (1) is used as at least one constituent material in the electron transport layer.

6. The organic electroluminescent device according to claim 4, wherein the organic layer is a hole blocking layer, and the compound represented by the general formula (1) is used as at least one constituent material in the hole blocking layer.

7. The organic electroluminescent device according to claim 4, wherein the organic layer is a light emitting layer, and the compound represented by the general formula (1) is used as at least one constituent material in the light emitting layer.

8. The organic electroluminescent device according to claim 4, wherein the organic layer is an electron injection layer, and the compound represented by the general formula (1) is used as at least one constituent material in the electron injection layer.

* * * * *